United States Patent
Springer et al.

(10) Patent No.: US 7,235,585 B2
(45) Date of Patent: Jun. 26, 2007

(54) ENZYME ACTIVATED SELF-IMMOLATIVE N-SUBSTITUTED NITROGEN MUSTARD PRODRUGS

(75) Inventors: Caroline J. Springer, Sutton (GB); Ion Niculescu-Duvaz, Sutton (GB); Dan M. Niculescu-Duvaz, Sutton (GB)

(73) Assignee: Cancer Research Technology Limited, London (GB)

( * ) Notice: Subject to any disclaimer, the term of this patent is extended or adjusted under 35 U.S.C. 154(b) by 21 days.

(21) Appl. No.: 10/526,173

(22) PCT Filed: Sep. 1, 2003

(86) PCT No.: PCT/GB03/03736

§ 371 (c)(1),
(2), (4) Date: Mar. 2, 2005

(87) PCT Pub. No.: WO2004/020400

PCT Pub. Date: Mar. 11, 2004

(65) Prior Publication Data

US 2006/0069154 A1 Mar. 30, 2006

(30) Foreign Application Priority Data

Sep. 2, 2002 (GB) ................................. 0220319.8

(51) Int. Cl.
*A01N 47/10* (2006.01)
*C07C 261/00* (2006.01)

(52) U.S. Cl. .................... 514/483; 560/133; 560/21
(58) Field of Classification Search ............... 560/134, 560/133, 21; 424/155; 604/892; 514/483
See application file for complete search history.

(56) References Cited

U.S. PATENT DOCUMENTS 6,005,002 A * 12/1999 Springer et al. ............ 514/483

FOREIGN PATENT DOCUMENTS

| WO | 90/02729 | 3/1990 |
|---|---|---|
| WO | 91/03460 | 3/1991 |
| WO | 94/25429 | 11/1994 |
| WO | 95/02420 | 1/1995 |
| WO | 95/03830 | 2/1995 |
| WO | 96/03151 | 2/1996 |
| WO | 96/03515 | 2/1996 |
| WO | 96/22277 | 7/1996 |
| WO | 9622277 A1 * | 7/1996 |
| WO | 97/26918 | 7/1997 |
| WO | 00/58271 | 10/2000 |
| WO | 02/060862 | 8/2002 |

OTHER PUBLICATIONS

Bagshawe et al., 1988, "A Cytotoxic Agent Can Be Generated Selectively At Cancer Sites," *British Journal of Cancer*, vol. 58, pp. 700-703.

Bagshawe et al., 1994, "Antibody-Directed Enzyme Prodrug Therapy (ADPET): A Review of Some Theoretical, Experimental and Clinical Aspects," *Analytical Oncology*, vol. 5, pp. 879-891, annals of oncology.

Denny and Wilson, 1998, "The Design of Selectively-Activated Anti-Cancer Prodrugs for Use in Antibody-Directed and Gene-Directed Enzyme Prodrug Therapies," *Journal of Pharmaceutical Pharmacology*, vol. 50, pp. 387-394.

Deonarain and Epenetos, 1994, "Targeting Enzymes for Cancer Therapy: Old Enzymes in New Roles," *British Journal of Cancer*, vol. 70, pp. 786-794.

Dowell et al., 1996, "New Mustard Prodrugs for Antibody-Directed Enzyme Prodrug Therapy: Alternative for the Amide Link," *Journal of Medicinal Chemistry*, vol. 39, pp. 1100-1105.

Encell and Loeb, 1998, "Improving Enzymes for Cancer Gene Therapy," *Tumor Targeting*, vol. 3, p. 191.

Ferenz, C. R., et al. 1989, *Journal of Labelled Compounds & Radiopharmaceuticals*, vol. 27, pp. 737-751.

(Continued)

*Primary Examiner*—Samuel A Barts
*Assistant Examiner*—Lalitha Nagubandi
(74) *Attorney, Agent, or Firm*—Nixon & Vanderhye P.C.

(57) ABSTRACT

This invention pertains to certain enzyme (CPG2) activated self-immolative nitrogen mustard prodrugs, which are useful in enzyme prodrug therapy (EPT), such as ADEPT and GDEPT, for the treatment of proliferative conditions, such as cancer, and which have the following formula:

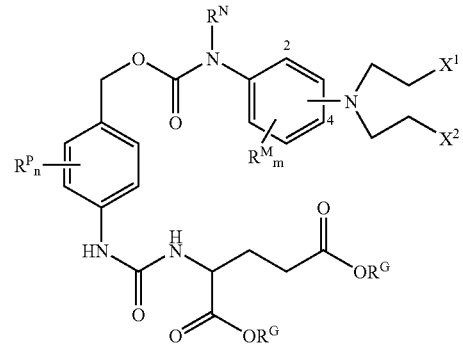

wherein: $R^N$ is independently $C_{1-7}$alkyl; $X^1$ is independently —I, —Br, or —Cl; $X^2$ is independently —I, —Br, or —Cl; the group —N(CH$_2$CH$_2$X$^1$)(CH$_2$CH$_2$X$^2$) is independently attached at the 2-position or at the 4-position; each $R^G$ is independently —H or an ester substituent; n is independently an integer from 0 to 4; each $R^P$, if present, is independently a phenyl substituent; m is independently an integer from 0 to 4; each $R^M$, if present, is independently a mustard substituent; and pharmaceutically acceptable salts, solvates, amides, and esters thereof. The present invention also pertains to pharmaceutical compositions comprising such compounds; such compounds and compositions for use in methods of treatment of the human or animal body by therapy; the use of such compounds and compositions for the manufacture of medicaments for the treatment of proliferative conditions; and the like.

53 Claims, No Drawings

OTHER PUBLICATIONS

Friedlos, F.; Davies, L.; Scanlon, I.; Ogilvie, L. M.; Martin, J.; Stribbling, S. M.; Niculescu-Duvaz, I.; Marais, R.; Springer, C. J., 2002, "Three new prodrugs for suicide gene therapy using CPG2 all elicit improved bystander effect efficacy in two xenograft models," *Cancer Research*, vol. 62, pp. 1724-1729.

Hay and Denny, 1996, "Antibody-Directed Enzyme Prodrug Therapy (ADEPT)," *Drugs of the Future*, vol. 21, pp. 917-931.

Jungheim and Shepherd, 1994, "Design of Antitumor Prodrugs: Substrates for Antibody Targeted Enzymes," *Chemical Reviews*, vol. 94, pp. 1553-1566.

Kirn, D., 2000, "Replication-selective microbiological agents fighting cancer with targeted germ ware," *Journal of Clinical Investigation (JCI)*, vol. 105, No. 7, pp. 837-839.

Marais, R.; Spooner, R. A.; Stribbling, S. M.; Light, Y.; Martin, J.; Springer, C. J. S., 1997, "A cell surface tethered enzyme improves efficiency in gene-directed enzyme prodrug therapy," *Nature Biotechnology*, vol. 15, pp. 1373-1377.

Martin, J.; Stribbling, S. M.; Poon, G. K.; Begent, R. H. J.; Napier, M.; Sharma, S. K.; Springer, C. J., 1997, "Antibody-directed enzyme prodrug therapy: Pharmacokinetics and plasma levels of prodrug and drug in a phase I clinical trial," *Cancer Chemotherapy and Pharmacology*, vol. 40, pp. 189-201.

Matthews, 1988, "Structural Basis of the Action of Thermolysin and Related Zinc Peptidases," *Accounts of Chemical Research*, vol. 21, pp. 333-340.

Melton and Sherwood, 1996, "Antibody-Enzyme Conjugates for Cancer Therapy," *Journal of the National Cancer Institute*, vol. 88, pp. 153-165.

Minton et al., 1984, "The Complete Nucleotide Sequence of the *Pseudomas* Gene Coding for Carboxypeptidase G2," *Gene*, vol. 31, pp. 31-38.

Napier, M. P.; Sharma, S. K.; Springer, C. J.; Bagshawe, K. D.; Green, A. J.; Martin, J.; Stribbling, S. M.; Cushen, N.; O'Malley, D.; Begent, R. H. J., 2000, "Antibody-directed enzyme prodrug therapy; Efficacy and mechanism of action in colorectal carcinoma," *Clinical Cancer Research*, vol. 6, pp. 765-772.

Niculescu-Duvaz and Springer, 1995, "Antibody-Directed Enzyme Prodrug Therapy (ADEPT): A Targeting Strategy in Chemotherapy," *Current Medicinal Chemistry*, vol. 2, pp. 687-706.

Niculescu-Duvaz and Springer, 1996, "Development of Prodrugs for ADEPT (Antibody-Directed Prodrug Therapy)," *Expert Opinion on Investigational Drugs*, vol. 3, pp. 289-308.

Niculescu-Duvaz and Springer, 1997, "Gene-Directed Enzyme Prodrug Therapy: A Review of Enzyme/Prodrug Combinations," *Expert Opinion on Investigational Drugs*, vol. 6, pp. 685-703.

Niculescu-Duvaz et al., 1998a, "Gene-Directed Enzyme Prodrug Therapy," *Bioconjugate Chemistry*, vol. 9, pp. 4-22.

Niculescu-Duvaz et al., 1999, "Prodrugs for antibody- and gene-directed enzyme prodrug therapies (ADEPT and GDEPT)", *Anti-Cancer Drug Design*, vol. 14, pp. 517-538.

Niculescu-Duvaz et al., 1999, "Self-Immolative Anthracycline Prodrugs for Suicide Gene Therapy", *J. Med. Chem.*, vol. 42, pp. 2485-2489.

Niculescu-Duvaz et al., 1999a, "Recent Developments in Gene-Directed Enzyme Prodrug Therapy (GDEPT) for cancer," *Current Opinion in Molecular Therapeutics*, vol. 1, pp. 480-486.

Niculescu-Duvaz et al., 2003, "Self-Immolative Nitrogen Mustard Prodrug Cleavable by Carboxypeptidase G2 (CPG2) Showing Large Cytotoxicity Differentials in GDEPT," *J. Med. Chem.*, vol. 46, No. 9, pp. 1690-1705.

Niculescu-Duvaz, D.; Niculescu-Duvaz, I.; Friedlos, F. F.; Martin, J.; Spooner, R.; Davies, L.; Marais, R.; Springer, C. J., 1998b, "Self-immolative mustard prodrugs for suicide gene therapy," *Journal of Medicinal Chemistry*, vol. 41, pp. 5297-5309.

Rowsell et al., 1997, "Crystal Structure of Carboxypeptidase G2, a Bacterial Enzyme with Applications in Cancer Therapy," *Structure*, vol. 5, pp. 337-347.

Roth and Cristiano, 1997, "Gene Therapy for Cancer: What Have We Done And Where Are We Going?," *Journal of the National Cancer Institute*, vol. 89, pp. 21-39.

Satchi and Duncan, 1998, "PDEPT: polymer-directed enzyme prodrug therapy," *British Journal of Cancer*, vol. 78, No. 2, pp. 149-150.

Senter et al., 1993, "Generation of Cytotoxic Agents by Targeted Enzymes," *Bioconjugate Chemistry*, vol. 4., pp. 3-9.

Sherwood et al., 1985, "Purification and Properties of Carboxypeptidase G2 *Pseudomonas* sp strain RS-16," *European Journal of Biochemistry*, vol. 148, pp. 447-453.

Spooner, R.; Martin, J.; Friedlos, F.; Marais, R.; Springer, C. J., 2000, "In suicide gene therapy, the site of subcellular localization of the activating enzyme is more important than the rate at which it activates prodrug," *Cancer Gene Therapy*, vol. 7, pp. 1348-1356.

Springer and Niculescu-Duvaz, 1995, "Antibody-Directed Enzyme Prodrug Therpay (ADEPT) with mustard prodrugs," *Anti-Cancer Drug Design*, vol. 10, pp. 361-362.

Springer and Niculescu-Duvaz, 1999, "Patent Property of Prodrugs Involving Suicide Gene Therapy," *Expert Opinion on Therapeutic Patents*, vol. 9, pp. 1381-1388.

Springer and Niculescu-Duvaz, 2000, "Prodrug-activating systems in suicide gene therapy", *The Journal of Clinical Investigation*, vol. 105, pp. 1161-1167.

Springer et al., 1990a, "Novel Prodrugs Which Are Activated to Cytotoxic Alkylating Agents by Carboxypeptidase G2," *Journal of Medicinal Chemistry*, vol. 33, pp. 677-681.

Springer et al., 1994, "Novel Prodrugs of Alkylating Agents Derived from 2-Fluoro- and 3-Fluorobenzoic Acids for Antibody-Directed Enzyme Prodrug Therapy", *Journal of Medicinal Chemistry*, vol. 37, pp. 2361-2370.

Springer et al., 1995a, "The Design of Prodrugs for Antibody Directed Enzyme Prodrug Therapy (ADEPT)," in *New Antibody Technologies and the Emergence of Useful Cancer Therapy*, Begent, R., Hamlin, A., editors (The Royal Society of Medicine Press: London), pp. 75-77.

Springer et al., 1995b, "Optimization of Alkylating Prodrugs Derived from Phenol and Aniline Mustards: A New Clinical Candidate Prodrug (ZD2767) for ADEPT," *Journal of Medicinal Chemistry*, vol. 38, pp. 5051-5065.

Wakselman, 1983, "1,4 and 1,6 Eliminations from Hydroxy-Amino-Substituted Benzyl Systems: Chemical and Biochemical Applications," *Nouveau Journal de Chemie*, vol. 7, pp. 439-447.

Zhang et al., 1995, "Advances in Cancer Gene Therapy," *Advances in Pharmacology*, vol. 12, pp. 289-341.

International Search Report of PCT/GB03/03736.

\* cited by examiner

ENZYME ACTIVATED SELF-IMMOLATIVE N-SUBSTITUTED NITROGEN MUSTARD PRODRUGS

This application is the US national phase of international application PCT/GB2003/003736 filed 1 Sep. 2003 which designated the U.S. and claims benefit of GB 0220319.8, dated 2 Sep. 2002, the entire content of which is hereby incorporated by reference.

TECHNICAL FIELD

This invention pertains generally to the field of chemotherapy, and more specifically to certain enzyme (CPG2) activated self-immolative nitrogen mustard prodrugs which are useful in enzyme prodrug therapy (EPT), such as ADEPT and GDEPT, for the treatment of proliferative conditions, such as cancer. The present invention also pertains to pharmaceutical compositions comprising such compounds; such compounds and compositions for use in methods of treatment of the human or animal body by therapy; the use of such compounds and compositions for the manufacture of medicaments for the treatment of proliferative conditions; and the like.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Chemotherapy

In general, cancer treatment by chemotherapy is limited by the need to deliver a high concentration of the anti-cancer drug selectively to the malignant cells. As a consequence, many methods for the efficient and selective delivery of a drug to the targeted malignant cells have been developed.

Many such methods employ prodrugs, which may be described, generally, as pharmacologically inactive (or relatively inactive) chemical derivatives of a drug molecule that require a transformation within the body in order to release the active drug.

In one approach, known as enzyme prodrug therapy (EPT), the transformation is effected by a particular enzyme, for example, carboxypeptidase G2 (CPG2) or nitroreductase (NR). Examples of such therapies include antibody directed enzyme prodrug therapy (ADEPT) and gene directed enzyme prodrug therapy (GDEPT), briefly described below.

Other enzyme prodrug therapies include ligand-directed enzyme prodrug therapy (LIDEPT) (see, e.g., Springer and Marais, 1997) and bacteria directed enzyme prodrug therapy (BDEPT) (see, e.g., Satchi and Duncan, 1998). See also, for example, Kirn, 2000.

ADEPT

The ADEPT approach separates the targeting from the cytotoxic functions in a two-step treatment. The selective component is an antibody (Ab) within an enzyme conjugate. The Ab binds antigen preferentially expressed on the surface of tumour cells. In the first step, the Ab-enzyme conjugate is administered and time is allowed for it to accumulate at the tumour and to clear from blood and normal tissues. In the second step, a non-toxic prodrug is administered that is converted specifically by the enzyme at the tumour into a low molecular weight toxic drug. The interstitial tumour transport of these low molecular weight cytotoxic agents thus generated is more favoured than those of large immunoconjugates such as immunotoxins. This allows greater tumour access for the toxic component. An amplification feature is inherent in ADEPT whereby one Ab-enzyme conjugate molecule can catalyse the conversion of many molecules of the prodrug into the cytotoxic drug, enabling higher concentrations of drug at the tumour than one-step Ab delivery systems. Another important factor is the by-stander effect, which effects killing of surrounding tumour cells even though they do not express tumour antigen or do not bind Ab-enzyme conjugate. The main drawback currently remains the immunogenicity of the Ab-enzyme conjugates which precludes the administration of repeated doses of the conjugate.

A number of papers review in detail the main features of ADEPT systems, including: Senter et al., 1993; Bagshawe et al., 1994; Deonarain and Epenetos, 1994; Jungheim and Shepherd, 1994; Niculescu-Duvaz and Springer, 1995, 1996; Springer and Niculescu-Duvaz, 1995; Springer et al., 1995a; Hay and Denny, 1996; Melton and Sherwood, 1996.

GDEPT

Gene therapy for cancer may be defined broadly as a genetic technology aimed at modifying either malignant or non-malignant cells for therapeutic gain. "Suicide" gene therapy approaches include GDEPT and VDEPT (virally directed enzyme prodrug therapy) (see, for example, Huber et al., 1995), the only difference between these approaches being that the former involves both viral and non-viral vectors.

Like ADEPT, GDEPT is a two-step treatment for tumours. Foreign enzymes are delivered to, and expressed in, target cells where they can activate subsequently administered non-toxic prodrugs to form active drugs. In the first step, a gene expressing the foreign enzyme is delivered. In the second step, a prodrug is administered that can be activated to form a toxic drug by the enzyme that has been expressed in the tumour. The foreign enzyme gene should be expressed exclusively, or with a relatively high ratio, in tumour cells compared with normal tissues and blood, and should achieve a sufficient concentration for clinical benefit. After gene delivery, prodrug administration must be delayed to permit protein expression in the targeted cells. The catalytic activity of the expressed protein should be sufficient for activation of the prodrug. Since expression of the foreign enzymes will not occur in all cells of a targeted tumour in vivo, a bystander cytotoxic effect is beneficial, whereby the prodrug is cleaved to an active drug that kills not only tumour cells but also neighbouring non-expressing tumour cells. This means that expression in less than 100% of tumour cells can still result in killing of all tumour cells. The foreign enzyme is usually expressed intracellularly, but by expressing the activating enzyme tethered to the outer cell surface of mammalian cells, potential advantages for GDEPT prodrug design are realized. The potential advantages of extracellular expression are twofold. Firstly, it should give an improved by-stander effect because the drug will be generated in the interstitial spaces within the tumour, rather than inside as with an intracellularly expressed activating enzyme. Secondly, the prodrug cannot enter cells to become activated and therefore non-cell-permeable prodrugs can be used. Thus, prodrugs which release drugs with intracellular targets may be rendered non-toxic by preventing their entry into cells. Upon activation, a potent and cell-permeable active moiety is released. This has already been demonstrated to be beneficial for prodrug-impermeable tumour cells (Marais et al., 1997). However, the potential for increased toxicity due to the diffusion of the active drug away from the tumour is a potential disadvantage, although this could also happen to active drugs from an intracellularly expressed enzyme.

A number of recent reviews cover the GDEPT approach, including: Zhang et al., 1995; Niculescu-Duvaz and Springer, 1997; Roth and Cristiano, 1997; Denny and Wilson, 1998; Encell and Loeb, 1998; Niculescu-Duvaz et al., 1998a, 1999; Springer and Niculescu-Duvaz, 1999a. Additional aspects are described in Springer and Marais, 1996a, 1996b.

Carboxypeptidase G2 (CPG2)

Peptidases are a class of enzymes (E) which act upon a substrate to cleave an amide linkage (—NH—C(=O)—) to give, usually, amino (—NH$_2$) and carboxylic acid (—C(=O)OH) products.

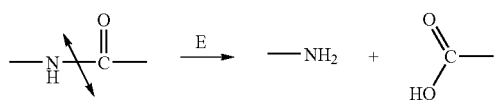

One peptidase of particular interest is carboxypeptidase G2 (referred to herein as "CPG2"). CPG2 is a bacterial enzyme isolated from Pseudomonas R16 (Sherwood et al., 1985). It is a zinc-dependent metallo-proteinase which exists as a homodimer molecule (2×41,800 Da) containing two Zn$^{2+}$ ions in each monomeric unit (Minton et al., 1984). The enzyme belongs to the group of calcium-binding zinc-endopeptidases from bacteria which contain thermolysin and other neutral peptidases from *Bacillus subtilis* and *Aeromonas proteolytica* (Matthews, 1988; Roswell et al., 1997).

CPG2 was first proposed by Bagshawe et al., 1988, and catalyses the scission of amidic (Springer et at., 1990a), urethanic or ureidic (Springer et al., 1995b; Dowell et al., 1996), bonds between a benzene nucleus and L-glutamic acid.

A preferred substrate for CPG2 is an L-glutamic acid group, linked to an aromatic ring via an amidic, carbamic, or ureidic linkage.

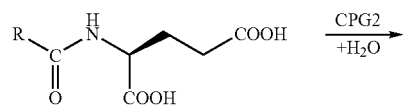

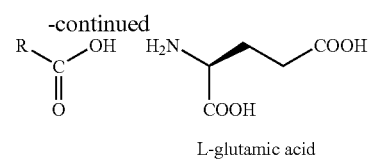

L-glutamic acid

However, glutamic acid analogs are also acceptable substrates. For example, L-glutamic acid modified at the γ-carbon (e.g., with an amide, —CONH$_2$, instead of an acid, —COOH) also serves as a suitable substrate for CPG2.

CPG2 is also tolerant as to whether the amide group is naked, or is part of a larger linkage, for example, a carbamate or a urea linkage.

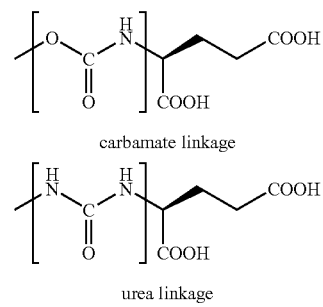

carbamate linkage urea linkage

For these compounds, CPG2 yields CO$_2$, L-glutamic acid, and R-ZH, wherein when Z is —O— (carbamates), R-ZH is a hydroxyl compound, R—OH, and when Z is —NH— (ureas), R-ZH is an amino compound, R—NH$_2$, where R is preferably an aromatic group.

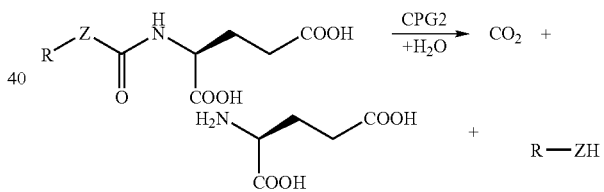

CPG2 Activated Self-Immolative Prodrugs

A "self-immolative prodrug" can be defined as a compound which, following an activation process, generates an unstable intermediate that releases the active drug in a number of subsequent steps.

Typically: (i) the activation process is of an enzymatic nature and is distinct from the extrusion step; (ii) the drug is generated by an extrusion process, following the fragmentation of the prodrug; (iii) the site of activation will normally be separated from the site of extrusion.

Potential advantages of self-immolative prodrugs include: the possibility of altering the lipophilicity of the prodrugs with minimal effect on the activation kinetics; the improvement of unfavourable kinetics of activation due to unsuitable electronic or steric features; the range of drugs which can be converted to prodrugs is greatly extended and is unrestricted by the structural substrate requirements for a given enzyme.

In one class of CPG2 activated self-immolative prodrugs, shown below, the L-glutamic acid and the active drug are separated by a 4-hydroxy (where Z is —O—) or 4amino where Z is —NH—) substituted benzylic spacer.

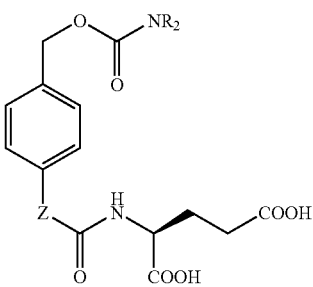

The activation of these prodrugs involves two steps:
(i) the cleavage of the oxycarbonyl- or carbamoyl-L-glutamyl linkage by CPG2, followed by the spontaneous decomposition of the carbonic or carbamic acid thus formed with loss of $CO_2$;
(ii) the fragmentation of the self-immolative intermediate by a 1,6-elimination mechanism (Wakselman, 1983), releasing a carbonic or carbamic acid which upon loss of $CO_2$ generates an active drug ($HNR_2$).

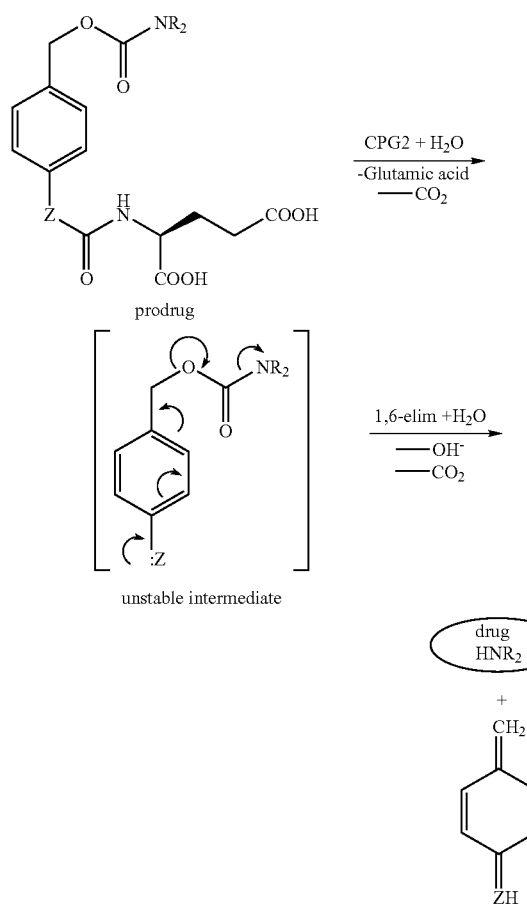

In this way, the prodrug, upon self-immolation, releases an amine drug (and $CO_2$) from a carbamate linkage. Other classes includes compounds which, upon self-immolation, release an aryl alcohol from an aryl ether; an aryl carboxylic acid from an aryl ester; an aryl alcohol (and $CO_2$) from an aryl carbonate; and the like. Similar self-immolative prodrugs are described, for example, in Springer et al, 1995c, 1995d.

Nitrogen Mustards

Nitrogen mustards are related to sulfur mustard, $(ClCH_2CH_2)_2S$, the "mustard gas" used during the First World War. Nitrogen mustards have the general formula $(ClCH_2CH_2)_2NR$. In vivo, each 2-chloroethyl side-chain undergoes an intramolecular cyclisation with the release of a chloride ion. The resulting highly reactive ethylene immonium derivative can interact with DNA and other molecules, for example, as an alkylating and/or crosslinking agent. Nitrogen mustards are useful, for example, in the treatment of proliferative conditions, such as cancer.

Nitrogen mustard analogues, in which the chloro group is replaced by other groups, such as other halogens (e.g., bromo, iodo) and other good leaving groups (e.g., sulfonates, such as mesyloxy, $—OSO_2Me$) are also known, and are included in the class denoted "nitrogen mustards."

Nitrogen mustards may conveniently be grouped according to the group R. For example, two groups are phenolic nitrogen mustards and anilinic nitrogen mustards.

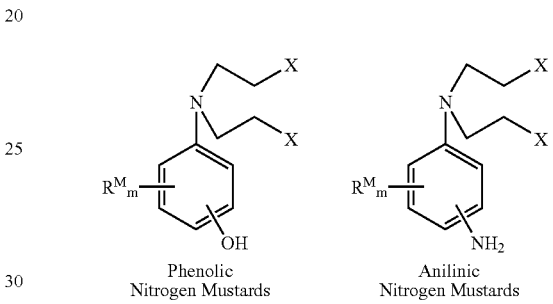

CPG2 Activated Nitrogen Mustard Prodrugs

The EPT approach has been applied to nitrogen mustard drugs. For example, in one approach, CPG2 acts upon the prodrug to yield a drug, R-ZH, which is a phenolic (Z is —O—) or anilinic (Z is —NH—) nitrogen mustard compound.

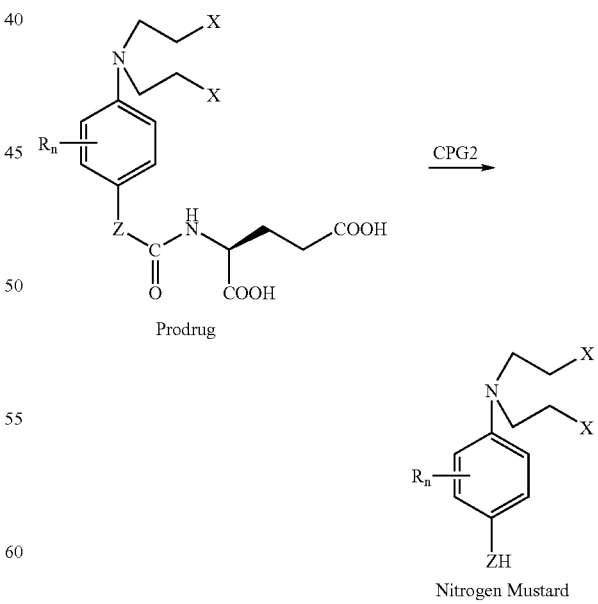

Various nitrogen mustard prodrugs are described, for example, in Springer 1990b, 1991, 1994, 2000, and 2002.

CPG2 Activated Nitrogen Mustard Self-Immolative Prodrugs

The CPG2 activated self-immolative prodrug approach, discussed above, has also been applied to nitrogen mustards. In one approach, the drug, $NHR_2$, is an anilinic nitrogen mustard compound. The prodrug is activated by CPG2, undergoes self-immolation, and releases the anilinic nitrogen mustard.

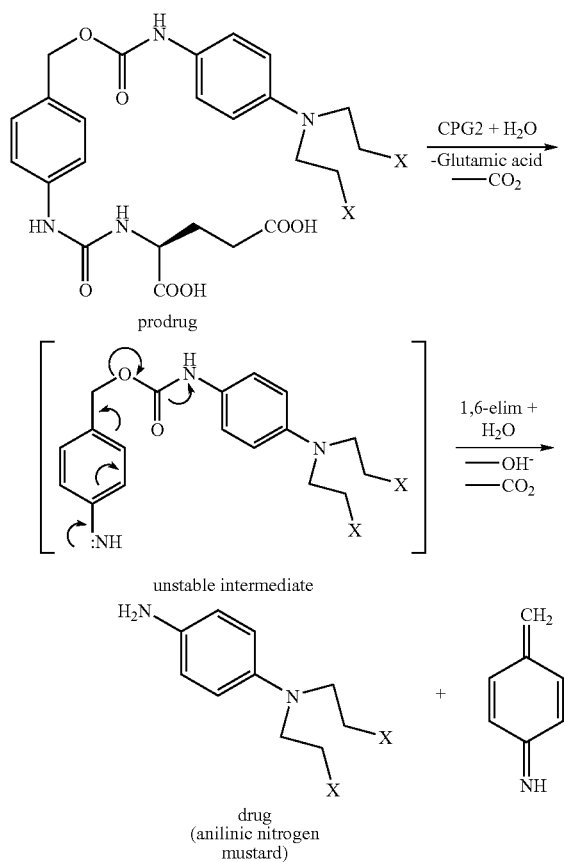

Springer et al, 1996, describe a number of nitrogen mustard prodrugs, including compounds of the following structure (see, for example, compounds 19 and 20 on pages 22 and 23 and in FIG. 3, therein).

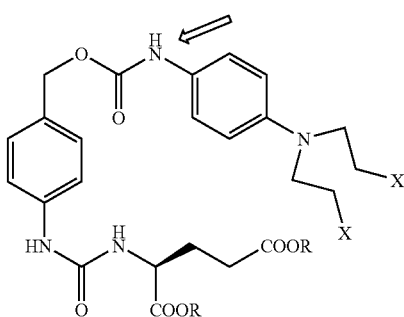

In each case, the nitrogen atom (indicated by the arrow, above) of the carbamate group which is between the benzyl group of the self-immolative core and the phenyl group of the nitrogen mustard is unsubstituted, that is, the carbamate group is —O—C(=O)—NH—. This nitrogen atom, identified as $Z^1$ therein, is soley described as —O— or —NH— (see page 3, line 5; page 6, line 24; page 7, line 1, page 7, line 7; page 11, line 1; and page 15 line 6, therein). Nowhere in this document is there provided any teaching or suggestion whatsoever that, as an alternative, the nitrogen atom of this carbamate group might be substituted.

The inventors have discovered that, surprisingly and unexpectedly, corresponding compounds, in which the nitrogen atom is substitued, for example, with a $C_{1-7}$alkyl group, offer one or more pharmacological advantages, including but not limited to: (a) improved activity; (b) improved selectivity (e.g., against tumour cells versus normal cells); (c) reduction in required dosage amounts; (d) reduction in required frequency of administration; (e) reduced intensity of undesired side-effects; (f) fewer undesired side-effects.

SUMMARY OF THE INVENTION

One aspect of the invention pertains to compounds (prodrugs), as described herein.

Another aspect of the present invention pertains to compounds (prodrugs) which (a) regulate (e.g., inhibit) cell proliferation; (b) inhibit cell cycle progression; (c) promote apoptosis; or (d) a combination of one or more of these.

Another aspect of the invention pertains to compounds (prodrugs), as described herein, which are anticancer agents.

Another aspect of the invention pertains to compounds (prodrugs), as described herein, which are antiproliferative agents.

Another aspect of the present invention pertains to a composition comprising a compound, as described herein, and a carrier.

Another aspect of the present invention pertains to a composition comprising a compound, as described herein, and a pharmaceutically acceptable carrier.

Another aspect of the present invention pertains to a method of (a) regulating (e.g., inhibiting) proliferation of a cell; (b) inhibiting cell cycle progression of a cell; (c) promoting apoptosis of a cell; or (d) a combination of one or more of these, in vitro or in vivo, comprising contacting the cell with an effective amount of a compound (prodrug), as described herein.

Another aspect of the present invention pertains to a method of regulating (e.g., inhibiting) proliferation of a cell, in vitro or in vivo, comprising contacting the cell with an effective amount of a compound (prodrug), as described herein.

Another aspect of the present invention pertains to a method of treatment, for example, of cancer, a proliferative condition, or other condition as described herein, comprising administering to a subject in need of treatment a therapeutically-effective amount of a compound (prodrug), as described herein, preferably in the form of a pharmaceutical composition.

Another aspect of the present invention pertains to a compound (prodrug) for use in a method of treatment of the human or animal body by therapy, for example, in the treatment of cancer, a proliferative condition, or other condition as described herein.

Another aspect of the present invention pertains to the use of a compound (prodrug) for the manufacture of a medicament, for example, for the treatment of cancer, a proliferative condition, or other condition as described herein.

Another aspect of the present invention pertains to a method for manufacturing a medicament intended for therapeutic application, for example, for the treatment of cancer, a proliferative condition, or other condition as described herein, characterised in that a compound (prodrug), as described herein, is used.

Another aspect of the invention pertains to a kit comprising (a) the compound (prodrug), preferably provided in a suitable container and/or with suitable packaging; and (b) instructions for use, for example, written instructions on how to administer the compound (prodrug), etc.

Another aspect of the present invention pertains to a method of enzyme prodrug therapy (EPT) which employs a compound (prodrug), as described herein, and a carboxypeptidase enzyme, as described herein.

Another aspect of the present invention pertains to a method of antibody directed enzyme prodrug therapy (ADEPT) which employs a compound (prodrug), as described herein, and a carboxypeptidase enzyme, as described herein.

Another aspect of the present invention pertains to a two component system (comprising two components for use in association with one another), comprising: (a) a prodrug, as described herein; and (b) an antibody or fragment thereof conjugated or fused to a carboxypeptidase enzyme, as described herein.

Another aspect of the present invention pertains to a method of gene directed enzyme prodrug therapy (GDEPT) which employs a compound (prodrug), as described herein, and a carboxypeptidase enzyme, as described herein.

Another aspect of the present invention pertains to a two component system (comprising two components for use in association with one another), comprising: (a) a prodrug, as described herein; and (b) a nucleic acid encoding (e.g., as part of a vector capable of expressing) a carboxypeptidase enzyme, as described herein.

Another aspect of the present invention pertains to compounds (e.g., intermediates, prodrugs, etc.) obtainable by a method of synthesis as described herein, or a method comprising a method of synthesis as described herein.

Another aspect of the present invention pertains to compounds (e.g., intermediates, prodrugs, etc.) obtained by a method of synthesis as described herein, or a method comprising a method of synthesis as described herein.

Another aspect of the present invention pertains to novel intermediates, as described herein (including, for example, compounds 7 and 8 in Scheme 2 and compounds 20, 21, 22, and 23 in Scheme 11), which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention pertains to compounds of the formula:

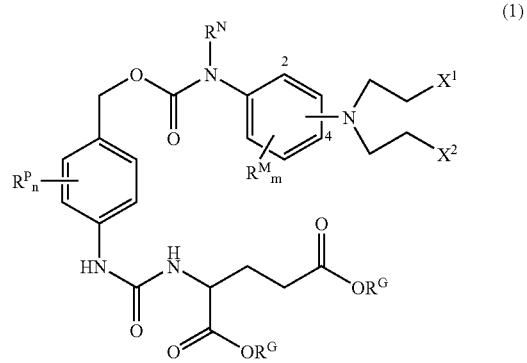

wherein:
$R^N$ is independently $C_{1-7}$alkyl;
$X^1$ is independently —I, —Br, or —Cl;
$X^2$ is independently —I, —Br, or —Cl;
the group —N(CH$_2$CH$_2$X$^1$)(CH$_2$CH$_2$X$^2$) is independently attached at the 2-position or at the 4-position;
each $R^G$ is independently —H or an ester substituent ($R^E$);
n is independently an integer from 0 to 4;
each $R^P$, if present, is independently a phenyl substituent;
m is independently an integer from 0 to 4;
each $R^M$, if present, is independently a mustard substituent;
and pharmaceutically acceptable salts, solvates, amides, and esters thereof.

Nitrogen Substituent, $R^N$

The nitrogen substituent, $R^N$, is independently $C_{1-7}$alkyl.

In one embodiment, $R^N$, is independently aliphatic $C_{1-7}$alkyl.

In one embodiment, $R^N$, is independently unsubstituted $C_{1-7}$alkyl.

In one embodiment, $R^N$, is independently unsubstituted aliphatic $C_{1-7}$alkyl.

In one embodiment, $R^N$ is independently $C_{1-4}$alkyl.

In one embodiment, $R^N$ is independently aliphatic $C_{1-4}$alkyl.

In one embodiment, $R^N$ is independently unsubstituted $C_{1-4}$alkyl.

In one embodiment, $R^N$ is independently unsubstituted aliphatic $C_{1-4}$alkyl.

In one embodiment, $R^N$ is independently -Me, -Et, -nPr, -iPr, -allyl, -nBu, -sBu, -iBu, or -tBu.

In one embodiment, $R^N$ is independently -Me or -Et.

In one embodiment, $R^N$ is independently -Me.

Mustard Substituents, $X^1$ and $X^2$

Each of the mustard substituents, $X^1$ and $X^2$, is independently —I, —Br, or —Cl.

In one embodiment, each of $X^1$ and $X^2$ is independently —I, —Br, or —Cl; and both of $X^1$ and $X^2$, are the same.

In one embodiment, each of $X^1$ and $X^2$ is independently —I or —Br.

In one embodiment, each of $X^1$ and $X^2$ is independently —I or —Br; and both of $X^1$ and $X^2$ are the same.

In one embodiment, each of X: and $X^2$ is independently —I.

In one embodiment, each of $X^1$ and $X^2$ is independently —Br.

In one embodiment, each of $X^1$ and $X^2$ is independently —Cl.

Position of the Nitrogen Mustard Group

The nitrogen mustard group, —N(CH$_2$CH$_2$X)$_2$, is independently attached at the 2-position ("ortho") or at the 4-position ("para").

In one embodiment, the nitrogen mustard group, —N(CH$_2$CH$_2$X$^1$)(CH$_2$CH$_2$X$^2$), is independently attached at the 2-position ("ortho").

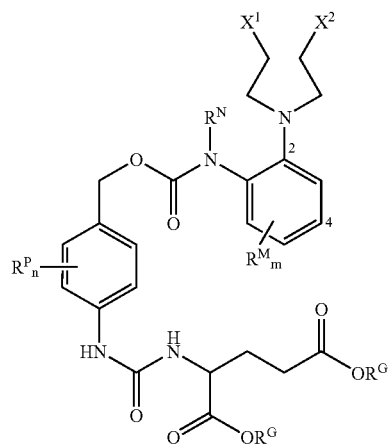

(2)

In one embodiment, the nitrogen mustard group, —N(CH$_2$CH$_2$X$^1$)(CH$_2$CH$_2$X$^2$), is independently attached at the 4-position ("para").

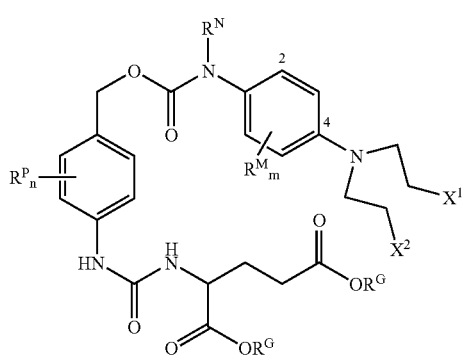

(3)

Phenyl Substituents, $R^P$

The phenylene group of the self-immolative core optionally bears phenyl substituents, $R^P$:

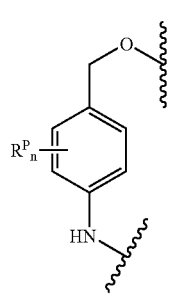

In one embodiment, n is 0, 1, 2, 3, or 4.
In one embodiment, n is 0, 1, 2, or 3.
In one embodiment, n is 0, 1, or 2.
In one embodiment, n is 0 or 1.
In one embodiment, n is 1, 2, 3, or 4.
In one embodiment, n is 1, 2, or 3.
In one embodiment, n is 1, or 2.
In one embodiment, n is 4.
In one embodiment, n is 3.
In one embodiment, n is 2.
In one embodiment, n is 1.
In one embodiment, n is 0.

In one embodiment, each $R^P$, if present, is independently halo, $C_{1-4}$alkyl, nitro, or cyano.

In one embodiment, each $R^P$, if present, is independently —F, —Cl, —Br, —I, -Me, -Et, -nPr, -iPr, -nBu, -sBu, -iBu, -tBu, —NO$_2$, or —CN.

In one embodiment, each $R^P$, if present, is independently —F, —Cl, —Br, or —I.

In one embodiment, each $R^P$, if present, is independently —F, —Cl or —Br.

In one embodiment, each $R^P$, if present, is independently —F or —Cl.

In one embodiment, each $R^P$, if present, is independently —F or —Br.

In one embodiment, each $R^P$, if present, is independently —F.

In one embodiment, the phenylene group has the following formula:

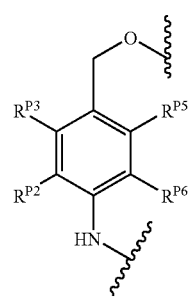

wherein each of $R^{P2}$, $R^{P3}$, $R^{P5}$, and $R^{P6}$ is independently —H or an phenyl substituent.

In one embodiment, each of $R^{P2}$, $R^{P3}$, $R^{P5}$, and $R^{P6}$ is independently —H or a phenyl substituent, as described above for $R^P$.

In one embodiment, each of $R^{P2}$ and $R^{P6}$ is —H (and each of $R^{P3}$ and $R^{P5}$ is other than —H, for example, as described above for $R^P$):

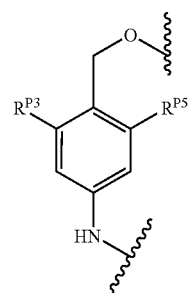

In one embodiment, each of $R^{P2}$, $R^{P5}$, and $R^{P6}$ is —H (and $R^{P3}$ is other than —H, for example, as described above for $R^P$):

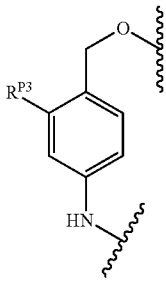

In one embodiment, each of $R^{P2}$, $R^{P3}$, $R^{P5}$, and $R^{P6}$ is —H.

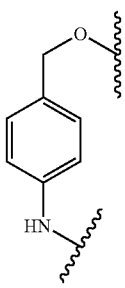

Mustard Substituents, $R^M$

The phenylene group, to which the nitrogen mustard group is attached, optionally also bears mustard substituents, $R^M$:

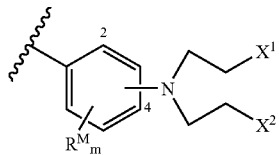

In one embodiment, m is 0, 1, 2, 3, or 4.
In one embodiment, m is 0, 1, 2, or 3.
In one embodiment, m is 0, 1, or 2.
In one embodiment, m is 0 or 1.
In one embodiment, m is 1, 2, 3, or 4.
In one embodiment, m is 1, 2, or 3.
In one embodiment, m is 1, or 2.
In one embodiment, m is 4.
In one embodiment, m is 3.
In one embodiment, m is 2.
In one embodiment, m is 1.
In one embodiment, m is 0:

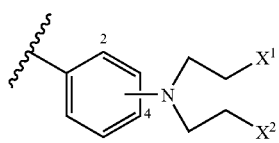

In one embodiment, each $R^M$, if present, is independently selected from:
  $C_{1-4}$alkyl (including, e.g., $C_{1-4}$haloalkyl);
  $C_{1-4}$alkoxy (including, e.g., $C_{1-4}$haloalkoxy);
  amino (including, e.g., di-$C_{1-4}$alkyl amino);
  halo;
  $C_{1-4}$alkylthio;
  acyl (e.g., $C_{1-7}$alkyl-acyloxy, $C_{5-6}$aryl-acyloxy);
  ester;
  amido;
  cyano;
  nitro; and,
  $C_{5-6}$aryl.

In one embodiment, each $R^M$, if present, is independently selected from:
  -Me, -Et, -nPr, -iPr, -nBu, -sBu, -iBu, -tBu;
  —$CF_3$, —$CH_2F$, —$CH_2CF_3$, —$CH_2CH_2F$; —$CF_2CF_3$;
  —OMe, —OEt, —O-nPr, —O-iPr, —O-nBu, —O-sBu, —O-iBu, —O-tBu;
  —$OCF_3$, —$OCH_2F$, —$OCH_2CF_3$, —$OCH_2CH_2F$; —$OCF_2CF_3$;
  —$NH_2$, —$NMe_2$, —$NEt_2$, —$N(nPr)_2$, —$N(iPr)_2$,
  —F, —Cl, —Br, —I;
  —SMe, —SEt;
  —C(=O)Me;
  —C(=O)OMe, —C(=O)OEt;
  —$CONH_2$, —CONHMe;
  —CN;
  —$NO_2$; and,
  -Ph.

In one embodiment, each $R^M$, if present, is independently selected from:
  $C_{1-4}$alkyl (including, e.g., $C_{1-4}$haloalkyl);
  $C_{1-4}$alkoxy (including, e.g., $C_{1-4}$haloalkoxy); and,
  amino (including, e.g., di-$C_{1-4}$-alkyl amino).

In one embodiment, each $R^M$, if present, is independently selected from:
  -Me, -Et, -nPr, -iPr, -nBu, -sBu, -iBu, -tBu;
  —$CF_3$, —$CH_2F$, —$CH_2CF_3$, —$CH_2CH_2F$; —$CF_2CF_3$;
  —OMe, —OEt, —O-nPr, —O-iPr, —O-nBu, —O-sBu, —O-iBu, —O-tBu;
  —$OCF_3$, —$OCH_2F$, —$OCH_2CF_3$, —$OCH_2CH_2F$; —$OCF_2CF_3$;
  —$NH_2$, —$NMe_2$, —$NEt_2$, —$N(nPr)_2$, and —$N(iPr)_2$, In one embodiment, each $R^M$, if present, is independently selected from:
  -Me, -Et, —$CF_3$, —OMe, —OEt, —$NH_2$, and —$NMe_2$.

In general, mustard substituents, $R^M$, which are electron-withdrawing and which decrease the chemical reactivity of the resulting nitrogen mustard are generally less preferred.

Glutamic Acid Ester Substituents, $R^G$

Each of the glutamic acid groups, $R^G$, is independently —H or an ester substiuent ($R^E$).

In one embodiment, each of the glutamic acid groups, $R^G$, is independently —H.

In one embodiment, each of the glutamic acid groups, $R^G$, is independently an ester substituent ($R^E$).

In one embodiment, each of the glutamic acid groups, $R^G$, is independently —H, unsubstituted $C_{1-7}$alkyl, substituted $C_{1-7}$alkyl, or silyl.

In one embodiment, each of the glutamic acid groups, $R^G$, is independently —H, unsubstituted $C_{1-7}$alkyl, or substituted $C_{1-7}$alkyl.

In one embodiment, each of the glutamic acid groups, $R^G$, is independently —H or unsubstituted $C_{1-7}$alkyl.

In one embodiment, the unsubstituted $C_{1-7}$alkyl group is independently unsubstituted $C_{1-4}$alkyl.

In one embodiment, the unsubstituted $C_{1-7}$alkyl group is independently: -Me, -Et, -nPr, -iPr, -allyl, -nBu, -sBu, -iBu, or -tBu.

In one embodiment, the substituted $C_{1-7}$alkyl group is independently $C_{1-7}$alkyl substituted with one or more groups selected from optionally substituted $C_{5-20}$aryl, $C_{1-7}$alkoxy, $C_{1-7}$alkylthio, and acyloxy.

In one embodiment, the substituted $C_{1-7}$alkyl group is independently $C_{1-4}$alkyl substituted with one or more groups selected from optionally substituted $C_{5-20}$aryl, $C_{1-7}$alkoxy, $C_{1-7}$alkylthio, and acyloxy.

In one embodiment, the substituted $C_{1-7}$alkyl group is independently $C_1$alkyl substituted with one or more groups selected from optionally substituted $C_{5-20}$aryl, $C_{1-7}$alkoxy, $C_{1-7}$alkylthio, and acyloxy.

In one embodiment, the substituted $C_{1-7}$alkyl group is independently $C_{1-7}$alkyl substituted with one or more groups selected from optionally substituted $C_{5-6}$aryl, $C_{1-4}$alkoxy, $C_{1-4}$alkylthio, $C_{1-4}$alkyl-acyloxy, $C_{5-6}$aryl-acyloxy.

In one embodiment, the substituted $C_{1-7}$alkyl group is independently $C_{1-4}$alkyl substituted with one or more groups selected from optionally substituted $C_{5-6}$aryl, $C_{1-4}$alkoxy, $C_{1-4}$alkylthio, $C_{1-4}$alkyl-acyloxy, $C_{5-6}$aryl-acyloxy.

In one embodiment, the substituted $C_{1-7}$alkyl group is independently $C_1$alkyl substituted with one or more groups selected from optionally substituted $C_{5-6}$aryl, $C_{1-4}$alkoxy, $C_{1-4}$alkylthio, $C_{1-4}$alkyl-acyloxy, $C_{5-6}$aryl-acyloxy.

In one embodiment, the substituted $C_{1-7}$alkyl group is independently $C_{1-7}$alkyl substituted with one or more groups selected from optionally substituted phenyl (e.g., methoxyphenyl, nitrophenyl), methoxy, methylthio, acetoxy, and benzoyloxy.

In one embodiment, the substituted $C_{1-7}$alkyl group is independently $C_{1-4}$alkyl substituted with one or more groups selected from optionally substituted phenyl (e.g., methoxyphenyl, nitrophenyl), methoxy, methylthio, acetoxy, and benzoyloxy.

In one embodiment, the substituted $C_{1-7}$alkyl group is independently $C_1$alkyl substituted with one or more groups selected from optionally substituted phenyl (e.g., methoxyphenyl, nitrophenyl), methoxy, methylthio, acetoxy, and benzoyloxy.

In one embodiment, the silyl group is independently —$SiR^S_3$, wherein each $R^S$ is independently —H or $C_{1-4}$alkyl.

In one embodiment, the silyl group is independently —Si(Me)$_3$, —Si(Et)$_3$, —Si(iPr)$_3$, —Si(tBu)(CH$_3$)$_2$, or —Si(tBu)$_3$.

In one embodiment, the silyl group is independently —Si(iPr)$_3$.

In one embodiment, each of the glutamic acid groups, $R^G$, is independently (1) t-butyl, (2) allyl, (3) tri-isopropylsilyl, (4) acetoxymethyl, (5) methoxymethyl, (6) methylthiomethyl, (7) p-methoxyphenylmethyl, (8) bis(o-nitrophenyl)methyl, (9) benzyl, or (10) diphenylmethyl.

In one embodiment, each of the glutamic acid groups, $R^G$, is independently (1) t-butyl, (2) allyl, (3) tri-isopropylsilyl, (4) acetoxymethyl, or (5) methoxymethyl.

In one embodiment, each of the glutamic acid groups, $R^G$, is independently (1) t-butyl, (2) allyl, or (3) tri-isopropylsilyl.

In one embodiment, each of the glutamic acid groups, $R^G$, is independently (1) t-butyl or (2) allyl.

In one embodiment, each of the glutamic acid groups, $R^G$, is independently (1) allyl.

Glutamic Acid Group Configuration

That part of the compound having the following formula is referred to herein as "the glutamic acid group":

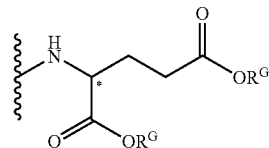

The carbon atom marked with an asterisk (*) is a chiral centre, and may be in an R or an S configuration.

In one embodiment, the carbon atom marked with an asterisk (*) is independently in an S configuration, and the glutamic acid group is an L-glutamic acid group, of the following formula:

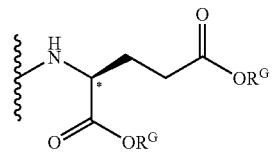

Certain Preferred Embodiments (1) In one embodiment:
(A1) $R^N$ is independently $C_{1-4}$alkyl; and,
(B1) each X is independently —Cl, —Br or —I.
(2) In one embodiment:
(A2) $R^N$ is independently -Et or -Me; and,
(B1) each X is independently —Cl, —Br or —I.
(3) In one embodiment:
(A3) $R^N$ is independently -Me; and,
(B1) each X is independently —Cl, —Br or —I.
(4) In one embodiment:
(A1) $R^N$ is independently $C_{1-4}$alkyl; and,
(B2) each X is independently —Br or —I.
(5) In one embodiment:
(A2) $R^N$ is independently -Et or -Me; and,
(B2) each X is independently —Br or —I.
(6) In one embodiment:
(A3) $R^N$ is independently -Me; and,
(B2) each X is independently —Br or —I.
(7) In one embodiment:
(A1) $R^N$ is independently $C_{1-4}$alkyl; and,
(B3) each X is independently —I.
(8) In one embodiment:
(A2) $R^N$ is independently -Et or -Me; and,
(B3) each X is independently —I.
(9) In one embodiment:
(A3) $R^N$ is independently -Me; and,
(B3) each X is independently —I.
(10) to (18): Each of the above embodiments (1) to (9), wherein furthermore:
(C1) the group —N(CH$_2$CH$_2$X)$_2$ is independently attached at the 4-position ("para").
(19) to (27): Each of the above embodiments (10) to (18), wherein furthermore:
(D1) n is independently 0.
(28) to (36): Each of the above embodiments (19) to (27), wherein furthermore:
(E1) m is independently 0.

(37) to (45): Each of the above embodiments (28) to (36), wherein furthermore:

(F1) $R^G$ is independently —H.

(46) to (54): Each of the above embodiments (28) to (36), wherein furthermore:

(F2) $R^G$ is independently $C_{1-6}$alkyl.

Specific Embodiments

In one embodiment, the compound is selected from the following compounds, and pharmaceutically acceptable salts, solvates, amides, and esters thereof:

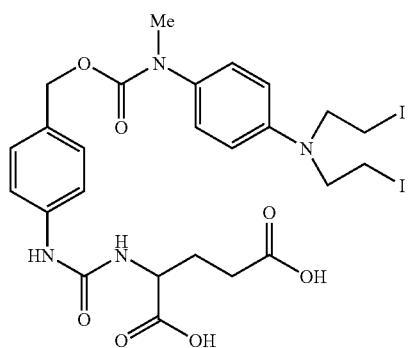

P-1

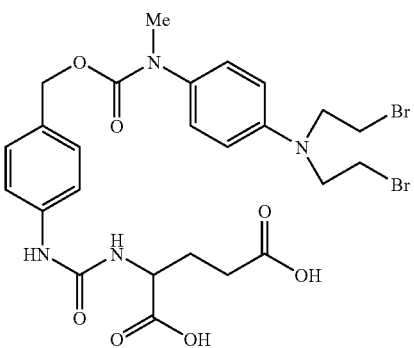

P-2

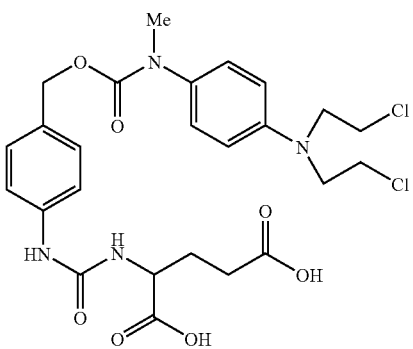

P-3

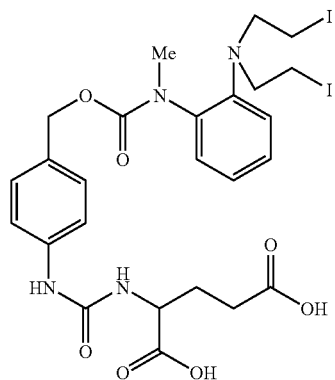

P-4

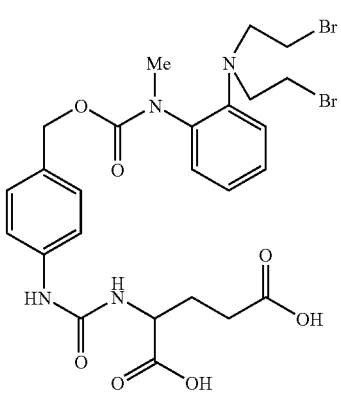

P-5

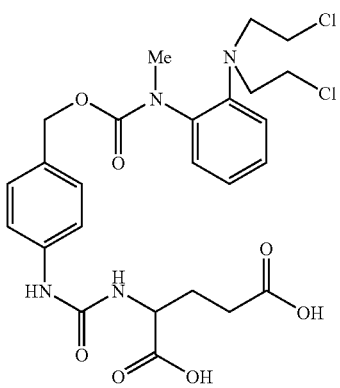

P-6

In one embodiment, the compound is selected from P-1, P-2, and P-3, and pharmaceutically acceptable salts, solvates, amides, and esters thereof.

In one embodiment, the compound is selected from P-1 and pharmaceutically acceptable salts, solvates, amides, and esters thereof.

In one embodiment, the compound is selected from P-2 and pharmaceutically acceptable salts, solvates, amides, and esters thereof.

In one embodiment, the compound is selected from P-3 and pharmaceutically acceptable salts, solvates, amides, and esters thereof.

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alklidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), norcarane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl, menthane, thujane, carane, pinane, bornane, norcarane, and camphene.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), aceanthrene ($C_{16}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (—C(CH$_3$)═CH$_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{1-4}$alkynyl, $C_{2-7}$alkynyl, $C_{2-20}$alkynyl.

Examples of (unsubstituted) unsaturated alkynyl groups include, but are not limited to, ethynyl (ethinyl, —C—CH) and 2-propynyl (propargyl, —CH$_2$—C≡CH).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl, and $C_{5-6}$heterocyclyl.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{3-12}$aryl, $C_{5-12}$aryl, $C_{5-7}$aryl, a $C_{5-6}$aryl.

The ring atoms may be all carbon atoms, as in "carboaryl groups" (e.g., $C_{5-20}$carboaryl).

Alternatively, the ring atoms may include one or more heteroatoms, as in "heteroaryl groups" (e.g., $C_{5-20}$heteroaryl).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substituents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N═ group may be substituted in the form of an N-oxide, that is, as —N(→O)═ (also denoted —N$^+$(→O$^-$)═). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (═O) groups on ring carbon atoms.

The above alkyl, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group.

Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): =O.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarbonyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

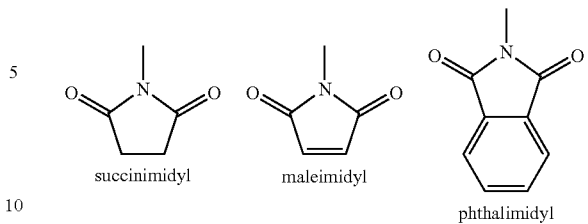

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Nitro: —NO$_2$.

Cyano (nitrile, carbonitrile): —CN.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH$_3$ and —SCH$_2$CH$_3$.

Silyl: —SiR$_3$, where R is a silyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of silyl groups include, but are not limited to, —SiH$_3$, —SiH$_2$(CH$_3$), —SiH(CH$_3$)$_2$, —Si(CH$_3$)$_3$, —Si(Et)$_3$, —Si(iPr)$_3$, —Si(tBu)(CH$_3$)$_2$, and —Si(tBu)$_3$.

In many cases, substituents may themselves be substituted. For example, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkoxy-$C_{5-20}$aryl group, e.g., as in anisole).

These and other specific examples of such substituted-substituents are described below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a "$C_{1-7}$perhaloalkyl group." Examples of $C_{1-7}$haloalkyl groups include, but are not limited to, —$CF_3$, —$CHF_2$, —$CH_2F$, —$CCl_3$, —$CBr_3$, —$CH_2CH_2F$, —$CH_2CHF_2$, and —$CH_2CF_3$.

$C_{1-7}$haloalkoxy: —OR, wherein R is a $C_{1-7}$haloalkyl group. Examples of $C_{1-7}$haloalkoxy groups include, but are not limited to, —$OCF_3$, —$OCHF_2$, —$OCH_2F$, —$OCCl_3$, —$OCBr_3$, —$OCH_2CH_2F$, —$OCH_2CHF_2$, and —$OCH_2CF_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —$CH_2OH$, —$CH_2CH_2OH$, and —$CH(OH)CH_2OH$.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —$CH_2COOH$ and —$CH_2CH_2COOH$.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —$CH_2NH_2$, —$CH_2CH_2NH_2$, and —$CH_2CH_2N(CH_3)_2$.

$C_{1-7}$aminoalkylamino: The term "$C_{1-7}$aminoalkylamino," as used herein, pertains to an amino group, —$NR^1R^2$, in which one of the substituents, $R^1$ or $R^2$, is itself a $C_{1-7}$aminoalkyl group (—$C_{1-7}$alkyl-$NR^1R^2$). The $C_{1-7}$aminoalkylamino may be represented, for example, by the formula —$NR^1$—$C_{1-7}$alkyl-$NR^1R^2$. Examples of amino-$C_{1-7}$alkylamino groups include, but are not limited to, groups of the formula —$NR^1(CH_2)_nNR^1R^2$, where n is 1 to 6, for example, —$NHCH_2NH_2$, —$NH(CH_2)_2NH_2$, —$NH(CH_2)_3NH_2$, —$NH(CH_2)_4NH_2$, —$NH(CH_2)_5NH_2$, —$NH(CH_2)_6NH_2$, —$NHCH_2NH(Me)$, —$NH(CH_2)_2NH(Me)$, —$NH(CH_2)_3NH(Me)$, —$NH(CH_2)_4NH(Me)$, —$NH(CH_2)_5NH(Me)$, —$NH(CH_2)_6NH(Me)$, —$NHCH_2NH(Et)$, —$NH(CH_2)_2NH(Et)$, —$NH(CH_2)_3NH(Et)$, —$NH(CH_2)_4NH(Et)$, —$NH(CH_2)_5NH(Et)$, and —$NH(CH_2)_6NH(Et)$.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (from toluene), xylyl (from xylene), mesityl (from mesitylene), and cumenyl (or cumyl, from cumene), and duryl (from durene).

$C_{1-7}$alkyl-$C_{5-20}$aryloxy: The term "$C_{1-7}$alkyl-$C_{5-20}$aryloxy," as used herein, describes certain $C_{5-20}$aryloxy groups which have been substituted with a $C_{1-7}$alkyl group. Examples of such groups include, but are not limited to, tolyloxy, xylyloxy, mesityloxy, cumenyloxy, and duryloxy.

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl, $PhCH_2$—), benzhydryl ($Ph_2CH$—), trityl (triphenylmethyl, $Ph_3C$—), phenethyl (phenylethyl, $Ph$-$CH_2CH_2$—), styryl (Ph-CH=CH—), cinnamyl (Ph-CH=CH—$CH_2$—).

$C_{5-20}$aryl-$C_{1-7}$alkoxy: The term "$C_{5-20}$aryl-$C_{1-7}$alkoxy," as used herein, describes certain $C_{1-7}$alkoxy groups which have been substituted with a $C_{5-20}$aryl group. Examples of such groups include, but are not limited to, benzyloxy, benzhydryloxy, trityloxy, phenethoxy, styryloxy, and cimmamyloxy.

$C_{5-20}$haloaryl: The term "$C_{5-20}$haloaryl," as used herein, describes certain $C_{5-20}$aryl groups which have been substituted with one or more halo groups. Examples of such groups include,-but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Includes Other Forms

Unless otherwise specified, included in the above are the well known ionic, salt, solvate, and protected forms of these substituents. For example, a reference to carboxylic acid (—COOH) also includes the anionic (carboxylate) form (—$COO^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—$O^-$), a salt or solvate thereof, as well as conventional protected forms.

Isomers, Salts, Solvates, Protected Forms, and Prodrugs

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms failing within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

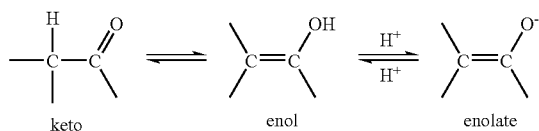

keto — enol — enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether, or an acetyl ester (—OC(=O)CH₃, —OAc).

For example, an aldehyde or ketone group may be protected as an acetal (R—CH(OR)₂) or ketal (R₂C(OR)₂), respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH₃); a benzyloxy amide (—NHCO—OCH₂C₆H₅, —NH—Cbz); as a t-butoxy amide (—NHCO—OC(CH₃)₃, —NH—Boc); a 2-biphenyl-2-propoxy amide (—NHCO—OC(CH₃)₂C₆H₄C₆H₅, —NH—Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH- Alloc), as a 2(-phenylsulphonyl)ethyloxy amide (—NH—Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a $triC_{1-7}$alkylsilyl-$C_{1-7}$alkyl ester; or a $C_{5-20}$aryl-$C_{1-7}$alkyl ester (e.g. benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

Synthesis

Several methods for the chemical synthesis of compounds of the present invention are described herein. These and/or other well known methods may be modified and/or adapted in known ways in order to facilitate the synthesis of additional compounds within the scope of the present invention.

In one approach, 2- or 4-fluoronitrobenzene (1) is reacted with diethanolamine (2) to form the corresponding 2- or 4-(di(2-hydroxyethyl)amino)nitrobenzene (3).

An example of such a method is illustrated in the following scheme, in which the conditions are: (i) heating at 130° C., without solvent, 16 h, 83%, purification by column chromatography (Kiselgel 60, eluent: AcOEt).

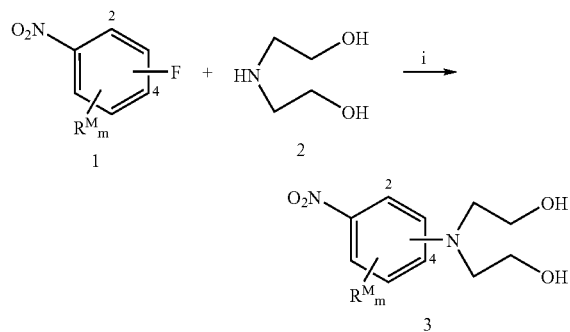

The hydroxy groups of the product (3) are protected as t-butyldimethylsilyl ethers (4). The nitro group is then reduced to give an amino group (5), which is first monoprotected, for example, as a benzyl carbamate (6), then substituted (e.g., alkylated) (7), and then deprotected to give the corresponding N-substituted product (8).

An example of such a method is illustrated in the following scheme, in which the conditions are: (i) t-butyl-dimethyl-silyl chloride (TBDMSiCl), imidazole, dimethyl formamide (DMF), room temperature (r.t.), 20 h, 89%; (ii) H$_2$, Pd/C (10%), THF, r.t., 6 h, 95%; (iii) N-benzyloxycarbonyloxy-succinimide, THF, r.t., 16 h, 95%; (iv) alkyl halide (e.g., alkyl iodide, e.g., methyl iodide), NaH, THF, r.t., 12 h, 100%; and (v) H$_2$, Pd/C 10%, AcOEt, r.t., 3 h, 100%.

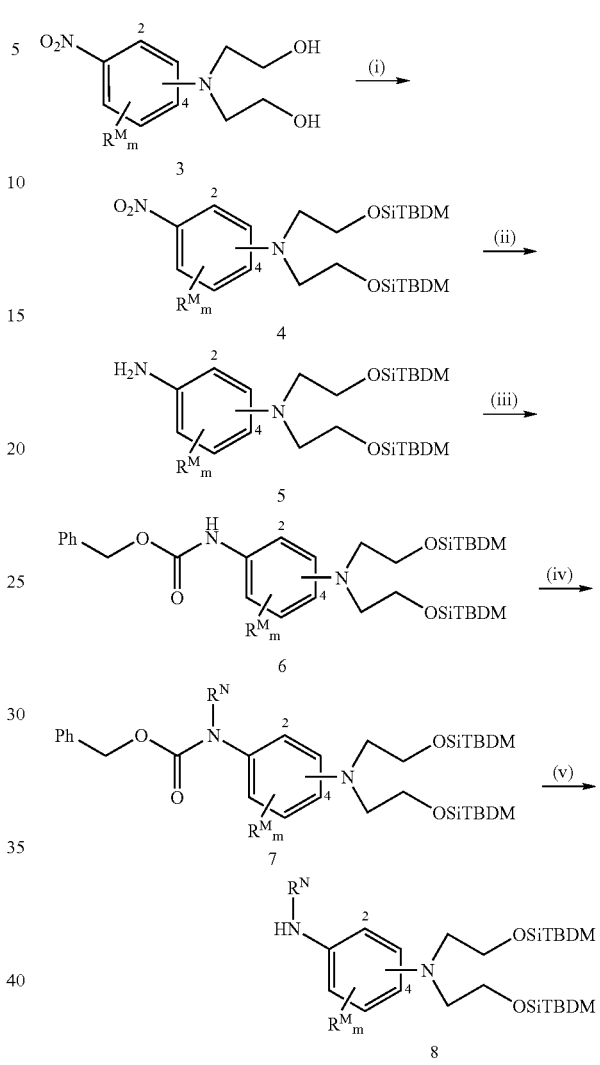

Another aspect of the present invention pertains to the intermediates 7 and 8 (and silyl analogs, —SiR$_3$, of —SiTBDM) in the above scheme, which are suitable for use in the methods of synthesis described herein. Another aspect of the present invention pertains to the use of such intermediates, as described herein, in the methods of synthesis described herein.

Separately, a linker compound (18), which incorporates the CPG2 substrate and the self-immolative core, is prepared, reacted with 4-nitrophenyl chloroformate to produce an activated linker (19), which was subsequently reacted with the N-substituted compound (8) (see below).

The linker compound (18) may be prepared, for example by reaction between an amine and an isocyanate.

In a first approach, (a), the self-immolative core reagent bears an amine (and has an unprotected hydroxy group) (9) and the glutamate reagent bears an isocyanate (16). The resulting product is the diester of the linker compound (18), which is then activated by formation of the corresponding glutamate-urea-benzyl-p-nitrophenylcarbonate (19).

In a second approach, (b), the self-immolative core reagent bears an amine (and has a protected hydroxy group) (12) and the glutamate reagent bears an isocyanate (16). The resulting product is the hydroxy-protected diester of the linker compound (17), which is then hydroxy-deprotected to give the diester of the linker compound (18), which is then converted to the reactive linker compound (19).

In a third approach, (c) the self-immolative core reagent bears an isocyanate (and has a protected hydroxy group) (13) and the glutamate reagent bears an amine (15). The resulting product is the hydroxy-protected diester of the linker compound (17), which is then hydroxy-deprotected to give the diester of the linker compound (18), which is then converted to the reactive linker compound (19).

4-aminobenzyl alcohols (9) (suitable for use in approach (a)) are available commercially (for example, from Lancaster; Fluka; etc.) or may be synthesised using well known methods.

Hydroxy-protected 4-aminobenzyl alcohols (12) (suitable for approach (b)) and hydroxy-protected 4-isocyanatobenzyl alcohols (13) (suitable for appro ach (c)) may be prepared as follows. The hydroxy group of optionally substituted p-nitrobenzyl alcohol (10) is first protected, for example, as a t-butyldiphenylsilyl ether or a 2-tetrahydropyranyl ether (11). The nitro group is then reduced to form an amino group (12), and the amino group is then converted to an isocyanato group (13).

An example of such a method is illustrated in the following scheme, in which the conditions are: (i) tert-butyldiphenylsilylchloride (TBDPSiCl) (then $R^1$ is —Si(tBu)(Ph)$_2$), imidazole, DMF (or THF); or 3,4-dihydropyran (then $R^1$ is 2-tetrahydropyranyl), pyridinium-p-toluene sulphonic acid (PPTS), $CH_2Cl_2$, room temperature; (ii) $H_2$, Pd/C (10%), $HCO_2NH_4$, EtOH; (iii) $(Cl_3CO)_2CO$, $NEt_3$, toluene, 70° C.

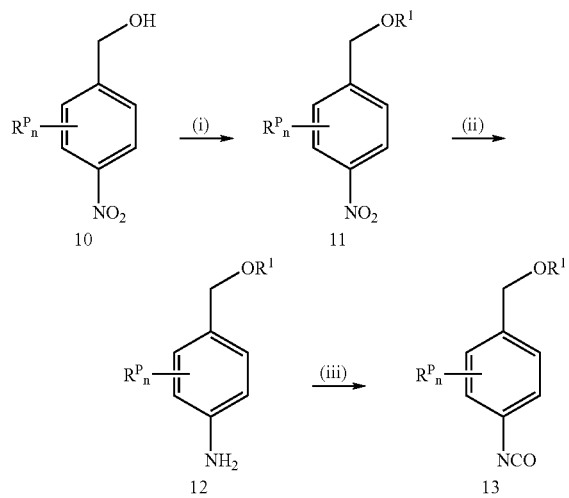

Separately, the acid groups of glumatic acid (14) are protected, for example, as ester groups (15), for example, as the di-allyl ester or the di-t-butyl ester, preferably as the di-allyl ester.

An example of such a method is illustrated in the following scheme, in which the conditions are suitable esterification conditions. For example, where $R^G$ is tBu, suitable conditions are: (i) isobutene, $H_2SO_4$, DCM, −70° C. to r.t., 16 h, 86% (the yield is better than the one reported in the literature; see, for example, Ferenz et al., 1989). Note also that the di-tBu ester is commercially available, but expensive (bis-t-Bu-L-glutamate, HCl salt, 25 g, £257, NovaBiochem UK, CN Biosciences (UK) Ltd.), and that the preferred di-allyl ester is commercially available and cheap (bis-allyl-L-glutamate, tosylate salt, 25 g, £64, NovaBiochem).

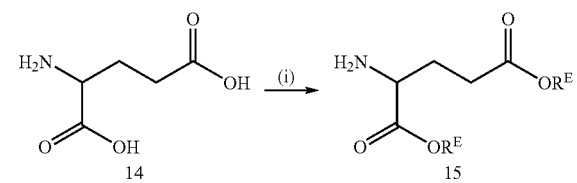

If necessary, the amino group of the protected glutamic acid (15) is converted to an isocyanato group (16) (suitable for approaches (a) and (b)).

An example of such a method is illustrated in the following scheme, in which the conditions are: (i) $(Cl_3CO)_2CO$, $NEt_3$, toluene or other aprotic solvent such as THF or dichloromethane (DCM), −78° C.

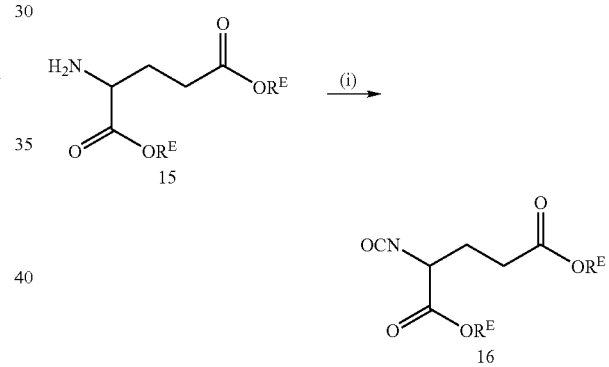

As described above, in approach (a), a self-immolative core reagent bearing an amine (and having an unprotected hydroxy group) (9) is reacted with a glutamate reagent bearing an isocyanate (16), to give the glutamate-urea-benzyl-ether (18).

An example of such a method is illustrated in the following scheme, in which the conditions are: (i) THF, $NEt_3$, room temperature.

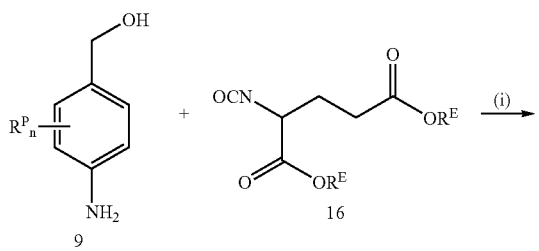

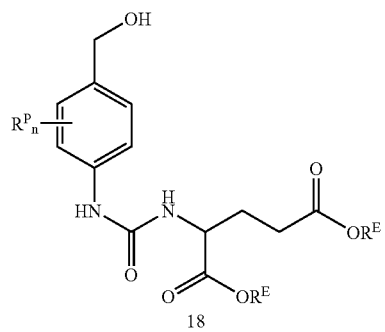

As described above, in approach (b), a self-immolative core reagent bearing an amine (and having a protected hydroxy group) (12) is reacted with a glutamate reagent bearing an isocyanate (16), to give the hydroxy-protected glutamate-urea-benzyl-ether (17).

An example of such a method is illustrated in the following scheme, in which the conditions are: (i) THF, NEt$_3$, room temperature.

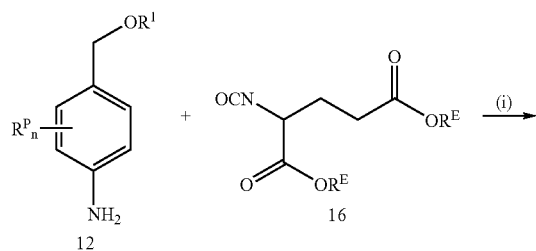

As described above, in approach (c), a self-immolative core reagent bearing an isocyanate (and having a protected hydroxy group) (13) is reacted with a glutamate reagent bearing an amine (15), to give the hydroxy-protected glutamate-urea-benzyl-ether (17).

An example of such a method is illustrated in the following scheme, in which the conditions are: (i) THF, NEt$_3$, room temperature.

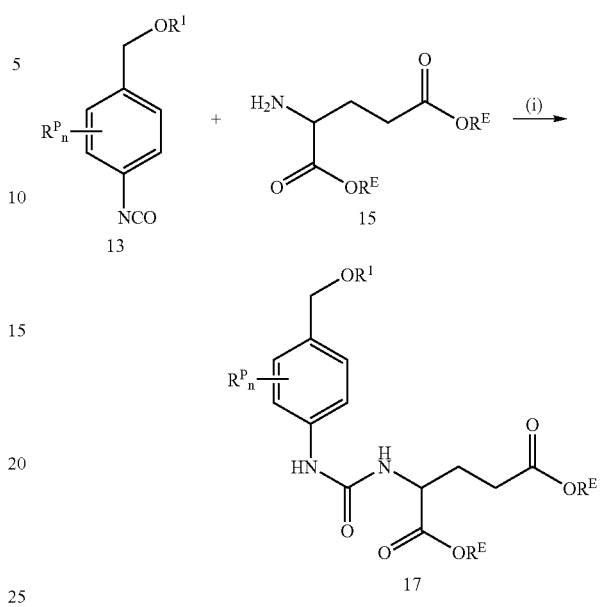

The hydroxy-protecting group of the hydroxy-protected glutamate-urea-benzyl-ether (17) is then removed using suitable deprotection conditions to yield the corresponding glutamate-urea-benzyl-alcohol (18).

An example of such a method is illustrated in the following scheme, in which suitable deprotection conditions may be used. For example, when $R^1$ is TBDPSi, the conditions are: (i) Bu$_4$NF, THF, room temperature; when $R^1$ is 2-tetrahydropyranyl (THP), the conditions are: (i) AcOH, THF, H$_2$O. Note that, when $R^1$ is TBDPSi, $R^E$ should not be allyl (but $R^E$ may be, e.g., t-butyl), because allyl ester-deprotection leads to undesired by-products; when $R^1$ is THP, such problems do not arise (and $R^E$ may be, e.g., allyl, t-butyl, etc.).

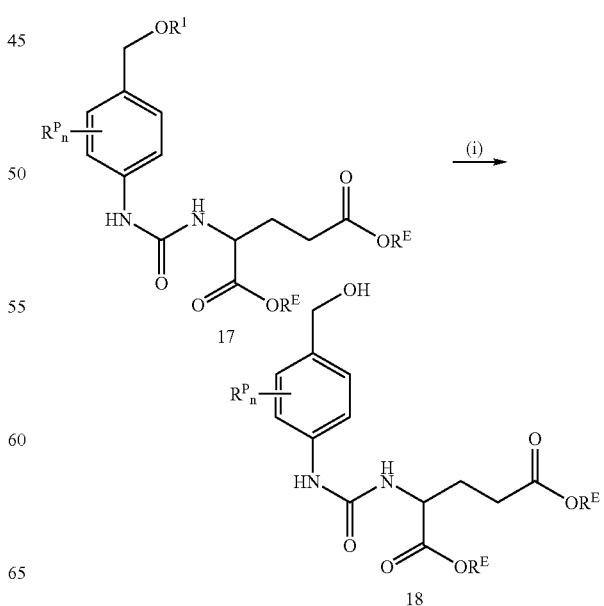

The glutamate-urea-benzyl-alcohol (18) is then activated by formation of the corresponding glutamate-urea-benzyl-p-nitrophenylcarbonate (19).

An example of such a method is illustrated in the following scheme, in which the conditions are: (i) 4-nitrophenyl-chloroformate, THF (or CH$_3$CN), NEt$_3$, room temperature, 1 h, 48–50%.

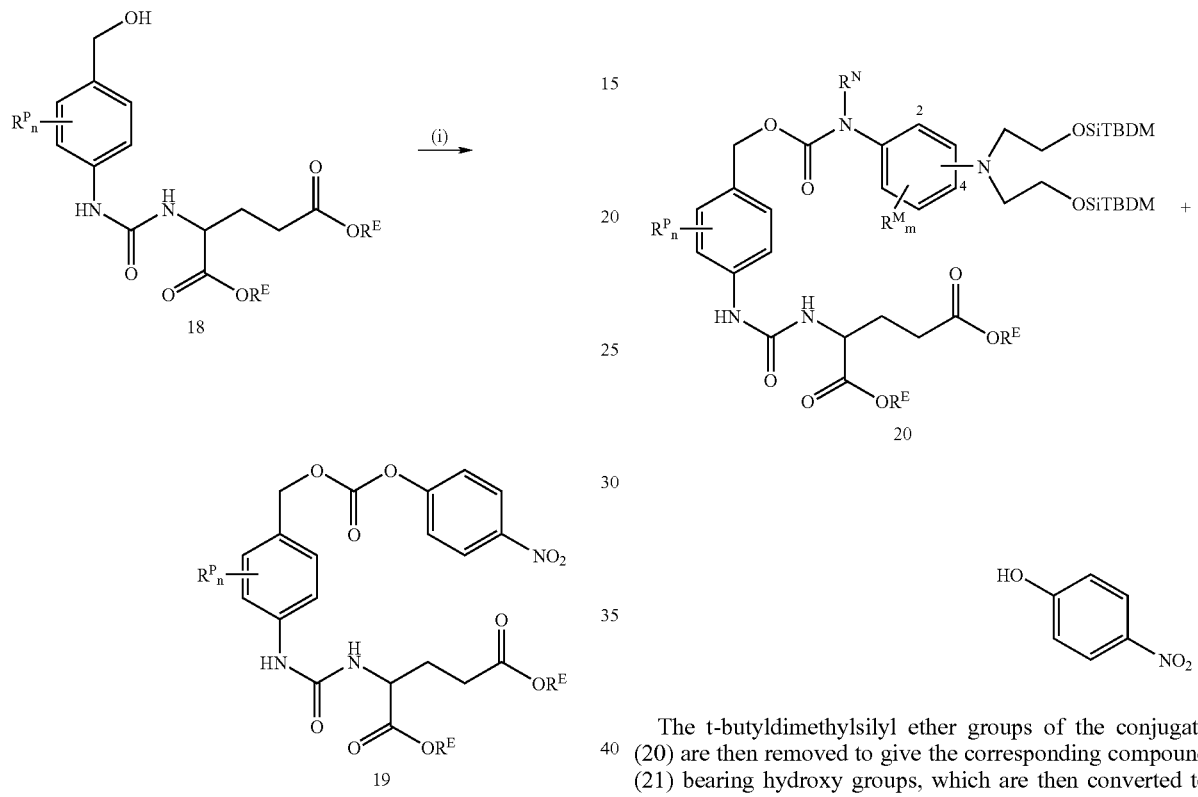

As described above, the reactive linker compound (19) is then reacted with the N-substituted compound (8), to form the conjugate (20).

An example of such a method is illustrated in the following scheme, in which the conditions are: (i) dimethyl acetamide (DMA), r.t., 5 days, 28%.

The t-butyldimethylsilyl ether groups of the conjugate (20) are then removed to give the corresponding compound (21) bearing hydroxy groups, which are then converted to sulfonates (e.g., mesylates) (22), and then to a halides (23).

An example of such a method is illustrated in the following scheme, in which the conditions are: (i) NEt$_3$.3HF, THF, r.t., 7 h, 97%; (ii) Mes$_2$O, NEt$_3$, 4-N,N-dimethylaminopyridine (DMAP), CH$_2$Cl$_2$, r.t., 2.5 h, 99%; and (iii) where X is I: NaI, acetone, reflux, 4 h, 94%; where X is Br: LiBr, THF, reflux, 1.5 h, 69%; and where X is Cl: LiCl, dimethyl acetamide (DMA), r.t., 24 h, 51%.

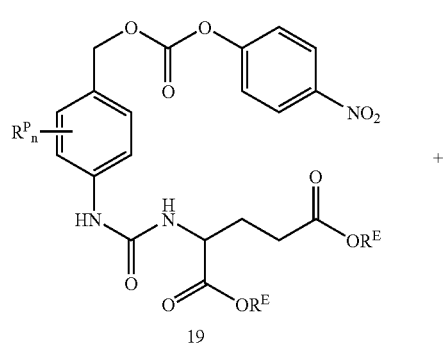

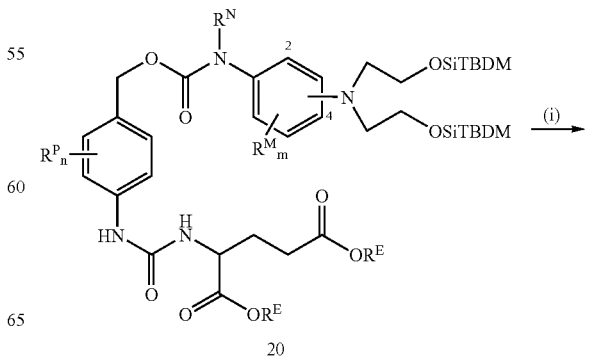

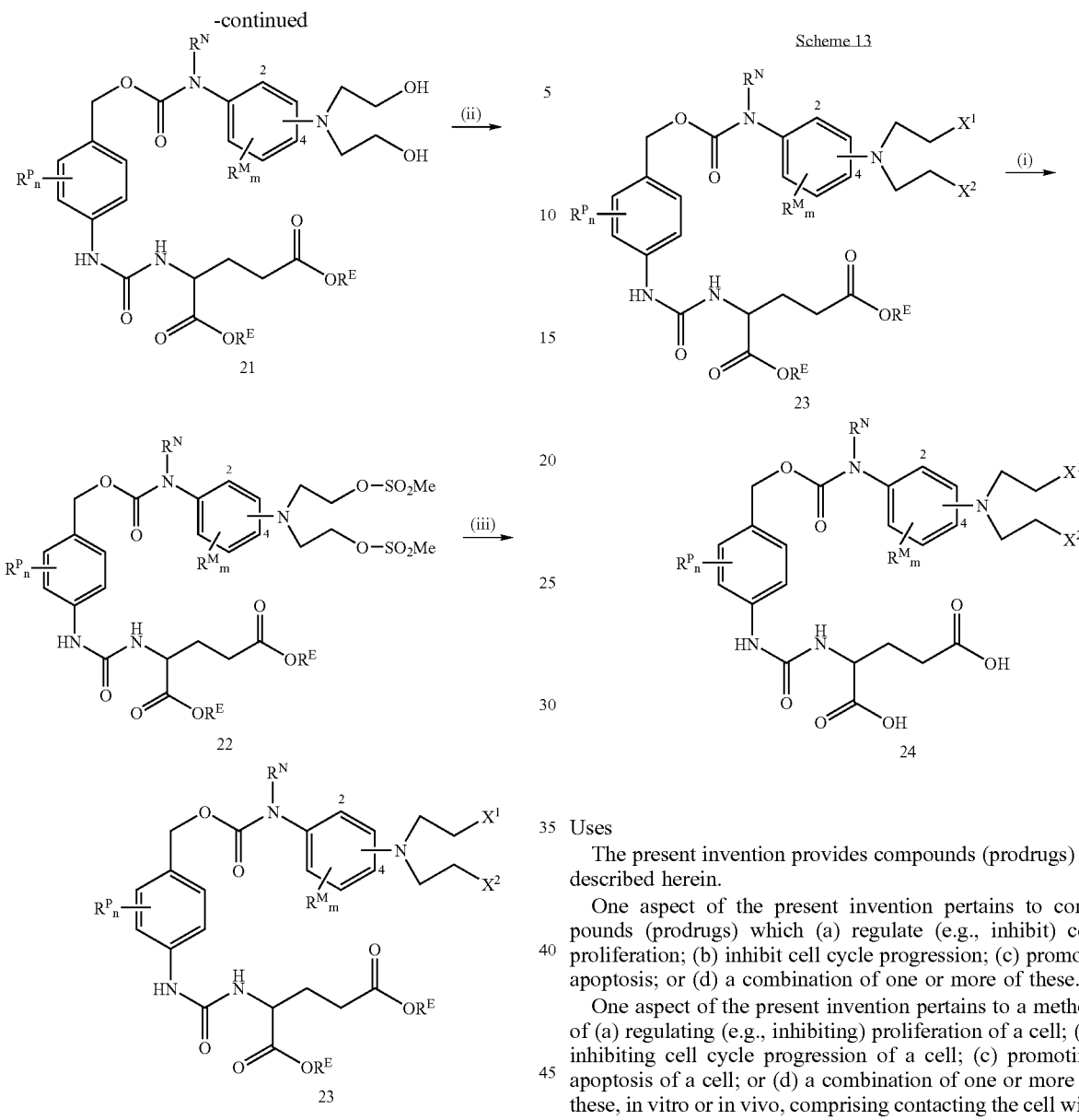

Another aspect of the present invention pertains to the intermediates 20, 21, 22, and 23 in the above scheme (and silyl, —SiR₃₁ analogs of —SiTBDM; and sulfonyl, —SO₂R, analogs of —SO₂Me), which are suitable for use in the methods of synthesis described herein.

Another aspect of the present invention pertains to the use of such intermediates, as described herein, in the methods of synthesis described herein.

The glutamic acid ester groups of the halide (23) are then removed using suitable deprotection conditions, to give the glutamic acid product (24).

An example of such a method is illustrated in the following scheme, in which suitable deprotection conditions are used. For example, where $R^G$ is allyl, the conditions are: (i) Pd(PPh₃)₄, morpholine or pyrrolidine, CH₂Cl₂, 50 min, then passed through an ion-exchange-column (e.g., Amberlite IRC50, weakly acidic), eluent MeOH, 84%.

Uses

The present invention provides compounds (prodrugs) as described herein.

One aspect of the present invention pertains to compounds (prodrugs) which (a) regulate (e.g., inhibit) cell proliferation; (b) inhibit cell cycle progression; (c) promote apoptosis; or (d) a combination of one or more of these.

One aspect of the present invention pertains to a method of (a) regulating (e.g., inhibiting) proliferation of a cell; (b) inhibiting cell cycle progression of a cell; (c) promoting apoptosis of a cell; or (d) a combination of one or more of these, in vitro or in vivo, comprising contacting the cell with an effective amount of a compound (prodrug), as described herein.

One aspect of the present invention pertains to a method of regulating (e.g., inhibiting) proliferation of a cell, in vitro or in vivo, comprising contacting the cell with an effective amount of a compound (prodrug), as described herein.

In one embodiment, the method is performed in vitro.

In one embodiment, the method is performed in vivo.

Preferably, the compound (prodrug) is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound (prodrug) are described in the examples below.

For example, a sample of cells (e.g., from a tumour) may be grown in vitro and a compound (prodrug) brought into contact with said cells, and the effect of the compound on those cells observed. As an example of "effect," the morphological status of the cells (e.g., alive or dead, etc.) may be determined. Where the active compound is found to exert an influence on the cells, this may be used as a prognostic or diagnostic marker of the efficacy of the compound in methods of treating a patient carrying cells of the same cellular type.

Methods of Treatment, Etc.

One aspect of the present invention pertains to a method of treatment, for example, of cancer, a proliferative condition, or other condition as described herein, comprising administering to a subject in need of treatment a therapeutically-effective amount of a compound (prodrug), as described herein, preferably in the form of a pharmaceutical composition.

One aspect of the present invention pertains to a compound (prodrug) for use in a method of treatment of the human or animal body by therapy, for example, in the treatment of cancer, a proliferative condition, or other condition as described herein.

One aspect of the present invention pertains to the use of a compound (prodrug) for the manufacture of a medicament, for example, for the treatment of cancer, a proliferative condition, or other condition as described herein.

One aspect of the present invention pertains to a method for manufacturing a medicament intended for therapeutic application, for example, for the treatment of cancer, a proliferative condition, or other condition as described herein, characterised in that a compound (prodrug), as described herein, is used.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of a compound (prodrug), or a material, composition or dosage form comprising a compound (prodrug), which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, enzyme prodrug therapy (EPT), such as GDEPT, ADEPT, etc.)); surgery; radiation therapy; and gene therapy.

Compound (prodrugs) may also be used, as described above, in combination therapies, that is, in conjunction with other agents, for example, cytotoxic agents.

Antiproliferative Applications

The present invention also provides compounds (prodrugs) which are antiproliferative agents.

The term "antiproliferative agent" as used herein, pertain to a compound which treats a proliferative condition (i.e., a compound which is useful in the treatment of a proliferative condition).

The terms "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

One of ordinary skill in the art is readily able to determine whether or not a candidate compound treats a proliferative condition for any particular cell type. For example, assays which may conveniently be used to assess the activity offered by a particular compound are described in the examples below.

Anticancer Applications

The present invention also provides compounds (prodrugs) which are anticancer agents.

The term "anticancer agent" as used herein, pertains to a compound (prodrug) which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Examples of cancers are discussed herein.

One of ordinary skill in the art is readily able to determine whether or not a candidate compound treats a cancerous condition for any particular cell type. For example, assays which may conveniently be used to assess the activity offered by a particular compound are described in the examples below.

Enzyme Prodrug Therapy Etc.

As discussed above, the compounds (prodrugs) described herein are useful in enzyme prodrug therapy (EPT) and related methods.

One aspect of the present invention pertains to a method of enzyme prodrug therapy (EPT) which employs a compound (prodrug), as described herein, and a carboxypeptidase enzyme, as described herein.

One aspect of the present invention pertains to a method of (a) regulating (e.g., inhibiting) proliferation of a cell; (b) inhibiting cell cycle progression of a cell; (c) promoting apoptosis of a cell; or (d) a combination of one or more of these, in vitro or in vivo, comprising contacting the cell with an effective amount of a compound (prodrug), as described herein, in the presence of a carboxypeptidase enzyme, as described herein.

One aspect of the present invention pertains to a method of regulating (e.g., inhibiting) proliferation of a cell, in vitro or in vivo, comprising contacting the cell with an effective amount of a compound (prodrug), as described herein, in the presence of a carboxypeptidase enzyme, as described herein.

One aspect of the present invention pertains to a method of treatment, for example, of cancer, a proliferative condition, or other condition as described herein, comprising administering to a subject in need of treatment a therapeutically-effective amount of a compound (prodrug), as described herein, preferably in the form of a pharmaceutical composition, in the presence of a carboxypeptidase enzyme, as described herein.

In one embodiment, the enzyme is a bacterial carboxypeptidase enzyme.

In one embodiment, the enzyme is CPG2.

In one embodiment, the enzyme is bacterial CPG2.

Examples of suitable carboxypeptidase enzymes, and methods for their preparation and use, are well known in the art. Guidance for the selection of additional suitable carboxypeptidase enzymes, and methods for their preparation and use, is also widely available. See, for example, the discussion above under the heading "Background," and the documents cited therein.

Antibody Directed Enzyme Prodrug Therapy Etc.

As discussed above, the compounds (prodrugs) described herein may be used in a method of antibody directed enzyme prodrug therapy (ADEPT) and related methods.

One aspect of the present invention pertains to a method of antibody directed enzyme prodrug therapy (ADEPT) which employs a compound (prodrug), as described herein, and a carboxypeptidase enzyme, as described herein.

One aspect of the present invention pertains to a two component system (comprising two components for use in association with one another), comprising: (a) a prodrug, as described herein; and (b) an antibody or fragment thereof conjugated or fused to a carboxypeptidase enzyme, as described herein.

One aspect of the present invention pertains to a two component system, as described above, for use in a method of treatment of the human or animal body by therapy.

One aspect of the present invention pertains to use of a two component system, as described above, for the manufacture of a medicament for the treatment of, for example, cancer, a proliferative condition, or other condition as described herein.

One aspect of the invention pertains to a kit comprising (a) a prodrug, as described herein; (b) an antibody or fragment thereof conjugated or fused to a carboxypeptidase enzyme, as described herein; and (c) instructions for use, for example, written instructions on how to perform ADEPT.

One aspect of the present invention pertains to a method of (a) regulating (e.g., inhibiting) proliferation of a cell; (b) inhibiting cell cycle progression of a cell; (c) promoting apoptosis of a cell; or (d) a combination of one or more of these, in vitro or in vivo, comprising: (i) contacting the cell with an antibody or fragment thereof conjugated or fused to a carboxypeptidase enzyme, as described herein; and (ii) contacting the cell with a therapeutically-effective amount of a compound (prodrug), as described herein, preferably in the form of a pharmaceutical composition.

One aspect of the present invention pertains to a method of regulating (e.g., inhibiting) proliferation of a cell, in vitro or in vivo, comprising: (i) contacting the cell with an antibody or fragment thereof conjugated or fused to a carboxypeptidase enzyme, as described herein; and (ii) contacting the cell with a therapeutically-effective amount of a compound (prodrug), as described herein, preferably in the form of a pharmaceutical composition.

One aspect of the present invention pertains to a method of treatment, for example, of cancer, a proliferative condition, or other condition as described herein, comprising administering to a subject in need of treatment: (i) an antibody or fragment thereof conjugated or fused to a carboxypeptidase enzyme, as described herein; and (ii) a therapeutically-effective amount of a compound (prodrug), as described herein, preferably in the form of a pharmaceutical composition.

Examples of suitable antibodies and antibody conjugates, and methods for their preparation and use, including methods of ADEPT, are well known in the art. Guidance for the selection of additional suitable antibodies and antibody conjugates, and methods for their preparation and use, is also widely available. See, for example, the discussion above under the heading "Background," and the documents cited therein.

Gene Directed Enzyme Prodrug Therapy Etc.

As discussed above, the compounds (prodrugs) described herein may be used in a method of gene directed enzyme prodrug therapy (GDEPT) and related methods.

One aspect of the present invention pertains to a method of gene directed enzyme prodrug therapy (GDEPT) which employs a compound (prodrug), as described herein, and a carboxypeptidase enzyme, as described herein.

One aspect of the present invention pertains to a two component system (comprising two components for use in association with one another), comprising: (a) a prodrug, as described herein; and (b) a nucleic acid encoding (e.g., as part of a vector capable of expressing) a carboxypeptidase enzyme,.as described herein.

One aspect of the present invention pertains to a two component system, as described above, for use in a method of treatment of the human or animal body by therapy.

One aspect of the present invention pertains to use of a two component system, as described above, for the manufacture of a medicament for the treatment of, for example, cancer, a proliferative condition, or other condition as described herein.

One aspect of the invention pertains to a kit comprising (a) a prodrug, as described herein; (b) a nucleic acid encoding (e.g., as part of a vector capable of expressing) a carboxypeptidase enzyme, as described herein; and (c) instructions for use, for example, written instructions on how to perform GDEPT.

One aspect of the present invention pertains to a method of (a) regulating (e.g., inhibiting) proliferation of a cell; (b) inhibiting cell cycle progression of a cell; (c) promoting apoptosis of a cell; or (d) a combination of one or more of these, in vitro or in vivo, comprising: (i) contacting the cell with a nucleic acid encoding (e.g., as part of a vector capable of expressing) a carboxypeptidase enzyme, as described herein; and (ii) contacting the cell with a therapeutically-effective amount of a compound (prodrug), as described herein, preferably in the form of a pharmaceutical composition.

One aspect of the present invention pertains to a method of regulating (e.g., inhibiting) proliferation of a cell, in vitro or in vivo, comprising: (i) contacting the cell with a nucleic acid encoding (e.g., as part of a vector capable of expressing) a carboxypeptidase enzyme, as described herein; and (ii) contacting the cell with a therapeutically-effective amount of a compound (prodrug), as described herein, preferably in the form of a pharmaceutical composition.

One aspect of the present invention pertains to a method of treatment, for example, of cancer, a proliferative condition, or other condition as described herein, comprising administering to a subject in need of treatment: (i) a nucleic acid encoding (e.g., as part of a vector capable of expressing) a carboxypeptidase enzyme, as described herein; and (ii) a therapeutically-effective amount of a compound (prodrug), as described herein, preferably in the form of a pharmaceutical composition.

Examples of suitable nucleic acids, vectors, and methods for their preparation and use, including methods of GDEPT, are well known in the art. Guidance for the selection of additional suitable vectors, and methods for their preparation and use, is also widely available. See, for example, the discussion above under the heading "Background," and the documents cited therein.

Additional Uses

The compounds (prodrugs) may also be used as cell culture additives, for example, in order to regulate (e.g., inhibit) cell proliferation in vitro.

The compounds (prodrugs) may also be used as part of an in vitro assay, for example, in order to determine whether a candidate host is likely to benefit from treatment with the compound in question.

The compounds (prodrugs) may also be used as a standard, for example, in an assay, in order to identify other compounds (prodrugs), other drugs, other anticancer agents, other antiproliferative agents, etc.

Routes of Administration

The compound (prodrug) or pharmaceutical composition comprising the compound (prodrug) may be administered to a subject by any convenient route of administration, whether systemically/ peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

In one embodiment, the subject is a prokaryote (e.g., bacteria) or a eukaryote (e.g., protoctista, fungi, plants, animals).

In one embodiment, the subject is an animal.

In one embodiment, the subject is a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

In one embodiment, the subject is a mammal.

In one embodiment, the subject is a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

In one embodiment, the subject is a human.

The subject may be any of its forms of development, for example, a spore, a seed, an egg, a larva, a pupa, or a foetus.

Formulations

While it is possible for the compound (prodrug) to be used (e.g., administered) alone, it is often preferable to present it as a formulation.

Thus, one aspect of the present invention pertains to a composition comprising a compound (prodrug), as described herein, and a carrier.

In one embodiment, the composition is a pharmaceutical composition (e.g., formulation, preparation, medicament) comprising a compound (prodrug), as described herein, and a pharmaceutically acceptable carrier.

In one embodiment, the composition is a pharmaceutical composition comprising at least one compound (prodrug), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 18th edition, Mack Publishing Company, Easton, Pa., 1990; and *Handbook of Pharmaceutical Excipients*, 2nd edition, 1994.

Another aspect of the present invention pertains to methods of making a pharmaceutical composition comprising admixing at least one compound (prodrug), as defined above, together with one or more other pharmaceutically acceptable ingredients well known to those skilled in the art, e.g., carriers, diluents, excipients, etc. If formulated as discrete units (e.g., tablets, etc.), each unit contains a pre-determined amount (dosage) of the compound (prodrug).

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the compound (prodrug) with a carrier which constitutes one or more accessory ingredients. In general, the formulations are prepared by uniformly and intimately bringing into association the compound (prodrug) with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in a the form of a depot or reservoir.

The compound (prodrug) may be dissolved in, suspended in, or admixed with one or more other pharmaceutically acceptable ingredients. The compound (prodrug) may be presented in a liposome or other microparticulate which is designed to target the compound (prodrug), for example, to blood components or one or more organs.

Formulations suitable for oral administration (e.g, by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the compound (prodrug) in a flavored basis, usually sucrose and acacia or tragacanth. Pastilles typically comprise the compound (prodrug) in an inert matrix, such as gelatin and glycerin, or sucrose and acacia. Mouthwashes typically comprise the compound (prodrug) in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or molding, optionally with one or more accessory ingredients. Compressed tablets may be prepared by compressing in a suitable machine the compound (prodrug) in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the compound (prodrug) therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound (prodrug) and a paraffinic or a water-miscible ointment base.

Creams are typically prepared from the compound (prodrug) and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound (prodrug) through the skin or other affected areas. Examples of such dermal penetration enhancers include dimethylsulfoxide and related analogues.

Emulsions are typically prepared from the compound (prodrug) and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the compound (prodrug) in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound (prodrug).

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound (prodrug) is dissolved or suspended in a suitable carrier, especially an aqueous solvent for the compound (prodrug).

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound (prodrug) is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound (prodrug) in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the compounds (prodrugs), and compositions comprising the compounds (prodrugs), can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the compound (prodrug) is in the range of about 0.1 to about 250 mg per kilogram body weight of the subject per day. Where the compound (prodrug) is a salt, a solvate, an ester, an amide, or the like, the amount administered is calculated on the basis of the parent compound and so the actual weight to be used is increased proportionately.

Kits

One aspect of the invention pertains to a kit comprising (a) the compound (prodrug), preferably provided in a suitable container and/or with suitable packaging; and (b) instructions for use, for example, written instructions on how to administer the compound (prodrug), etc.

The written instructions may also include a list of indications for which the compound (prodrug) is a suitable treatment.

EXAMPLES

The following are examples are provided solely to illustrate the present invention and are not intended to limit the scope of the invention, as described herein.

All starting materials, reagents and anhydrous solvents (eg. THF packed under $N_2$) were purchased from Aldrich, unless otherwise stated. Kieselgel 60 (0.043–0.060) was used in gravity columns (Art 9385 and 15111, Merck). TLC was performed on precoated sheets of Kieselgel 60 $F_{254}$ (Art 5735, Merck). Melting points were determinated on a Kofler hot-stage (Reichert Thermovar) melting point apparatus and are uncorrected. Low resolution EI and FAB spectra were performed on a VG-2AB-SE double focusing magnetic sector mass spectrometer (Fisons Instruments, Warrington, Manchester, UK), operating at a resolution of 1000.High resolution accurate mass spectra were determined on the same system, but with a resolution set to 8,000–10,000. Masses are measured by peak matching the unknown with a mass of known composition. Reported spectra are by FAB unless otherwise stated. NMR spectra were determined in $Me_2SO-d_6$ on a Brucker AC250 spectrometer (250 MHz) at 30° C. (303 K) unless otherwise stated. IR spectra (film) were recorded on a Perkin Elmer 1720X FT-IR spectrometer. Elemental analysis were determined by Butterworth Laboratories Ltd. (Teddington, Middlesex, UK) and are within 0.4% of theory except when stated. The chemical stability of the prodrugs and their propensity to behave as substrates for CPG2 were determined by HPLC.

Example 1

4-nitro-[bis(2'-hydroxyethyl)]-aniline (X-3a)

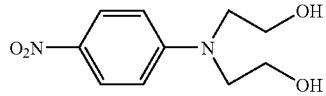

4-Nitrofluorobenzene (16.5 g, 11.7 mmol) was mixed with diethanolamine (35 mL) and the mixture was heated at 130° C. and stirred for 16 h. The reaction mixture was cooled to 60° C., then poured into a beaker containing NaOH (6 g) in water (1 L). The yellow precipitate was recovered by filtration and dried in dessicator for 24 h over $P_2O_5$, to afford the title compound (22 g, 83%) as a yellow solid.

$^1$H-NMR $\delta_H$ (ppm) 3.52–3.64 (m, 8H, N(CH$_2$, CH$_2$)$_2$OH), 4.82 (t, 2H, OH, J=5.29 Hz), 6.82 (d, 2H, $H_{arom2+6}$, J=9.58 Hz), 8.01 (d, 2H, $H_{arom3+5}$).

Example 2

4-Nitro-bis[2'-(tert-butyldimethylsilyloxy)ethyl]-aniline (X-4a)

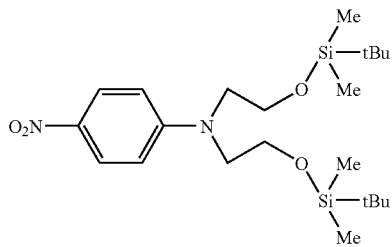

4-Nitro-[bis(2'-hydroxyethyl)]-aniline (X-3a) (5.0 g, 22.1 mmol) and tert-butyldimethylsilyl chloride (7.5 g, 50 mmol) were dissolved in 20 mL DMF; imidazole (4.76 g, 70 mmol) was added, and the solution stirred at room temperature for 20 h. The solution was then concentrated and purified by column chromatography (cyclohexane:AcOEt 1:1) to afford the title compound (8.9 g, 89%) as an yellow oil.

$^1$H-NMR $\delta_H$ (ppm): –0.03 (s, 12H, Si—CH$_3$), 0.81 (s, 18H, Si-t-Bu), 3.64 (t, 4H, NCH$_2$, J=5.19 Hz), 3.78 (t, 4H, CH$_2$OSi), 6.83 (d, 2H, $H_{arom2+6}$, J=9.37 Hz), 8.00 (d, 2H, $H_{arom3+5}$); MS m/z: 455 (M$^+$+1, 88), 477 (M$^+$+23, 5), 439 (M$^+$-Me, 53), 397 (M$^+$-t-Bu, 30); acc. mass: (C$_{22}$H$_{43}$N$_2$O$_4$Si$_2$) calcd. 455.2761, found 455.2767. Anal. (C$_{22}$H$_{43}$N$_2$O$_4$Si$_2$) C, H, N.

Example 3

2-nitro-[bis(2'-hydroxyethyl)]-aniline (X-3b)

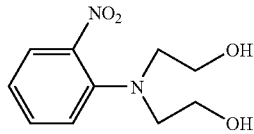

2-Nitrofluorobenzene (16.5 g, 11.7 mmol) was mixed with diethanolamine (35 mL) and the mixture was heated at 130° C. and stirred for 16 h. The reaction mixture was cooled to 60° C., then poured into a beaker containing NaOH (6 g) in water (1 L). The yellow precipitate was recovered by filtration and dried in dessicator for 24 h over $P_2O_5$, to afford the title compound as a yellow solid. After purification on column (Kiselgel 60, 0.040–0.063, eluent: AcOEt) a yield of 61% (16.66 g) was obtained.

$^1$H-NMR $\delta_H$ (ppm): 3.20 (t, 4H, —NHCH$_2$), 3.46 (t, 4H, CH$_2$OH), 4.54 (s, 2H, OH), 6.64 (t, 1H, $H_{arom4(5)}$), 7.39 (d, 1H, $H_{arom3(6)}$), 7.49 (t, 1H, $H_{arom5(4)}$), 7.68 (d, 1H, $H_{arom6(3)}$).

Example 4

2-Nitro-bis[2'-(tert-butyldimethylsilyloxy)ethyl]-aniline (X-4b)

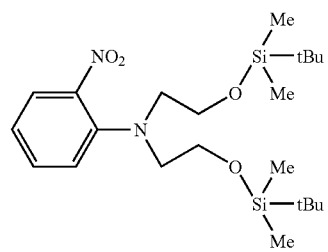

The title compound was prepared using 2-nitro-[bis(2'-hydroxyethyl)]-aniline (X-3b) in a method analogous to that described in the previous Example. The product was purified by column chromatography (eluent: cyclohexane:AcOEt 3:1) and obtained as a yellow oil (95%).

$^1$H-NMR $\delta_H$ (ppm): –0.03 (s, 12H, Si—CH$_3$), 0.80 (s, 18H, Si-t-Bu), 3.27 (t, 4H, NCH$_2$, J=5.87 Hz), 3.65 (t, 4H, CH$_2$OSi), 6.98 (dt, 1H, H$_5$, J=7.58 Hz), 7.37 (dd, 1H, H$_3$, J=8.43 Hz), 7.48 (dt, 1H, H$_4$, J=7.80 Hz), 7.67 (dd, 1H, H$_6$, J=8.05 Hz); MS m/z: 455 (M$^+$+1, 32), 397 (M$^+$-t-Bu, 8), 309 (M$^+$-SiTBDM, 100); acc. mass: (C$_{22}$H$_{43}$N$_2$O$_4$Si$_2$) calcd. 455.2761, found 455.2745. Anal. (C$_{22}$H$_{43}$N$_4$O$_4$Si$_2$) C, H; N required 6.17, found 6.94%.

Example 5

4-Amino-bis[2'-(tert-butyldimethylsilyloxy)ethyl]-aniline (X-5a)

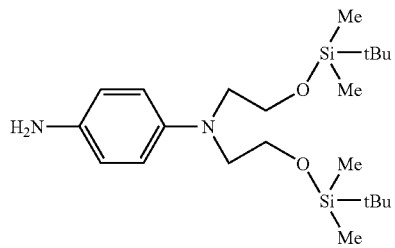

4-Nitro-bis[2'-(tert-butyldimethylsilyloxy)ethyl]-aniline (X-4a) (5.50 g, 12.1 mmol) was dissolved in 90 mL THF, 1.5 g Pd/C 10% was added, and the suspension was stirred under H$_2$ atmosphere for 6 h. The catalyst was then filtered off, the solvent evaporated and the residue purified by column chromatography (cyclohexane:AcOEt 3:1) to yield the title compound (4.90 g, 95%) as an oil.

$^1$H-NMR $\delta_H$ (ppm): 0.00 (s, 12H, Si—CH$_3$), 0.85 (s, 18H, Si-t-Bu), 3.30 (t, 4H, NCH$_2$, J=6.20 Hz), 3.63 (t, 4H, CH$_2$OSi—), 4.34 (s, 2H, NH$_2$), 6.46 (s, 4H, H$_{arom}$); MS m/z: 424 (M$^+$, 70); acc. mass: (C$_{22}$H$_{44}$N$_2$O$_2$Si$_2$) calcd. 424.2941, found 424.2950. Anal. (C$_{22}$H$_{44}$N$_2$O$_2$Si$_2$): H, N; C required 62.21, found 62.63%.

Example 6

2-Amino-bis[2'-(tert-butyldimethylsilyloxy)ethyl]-aniline (X-5b)

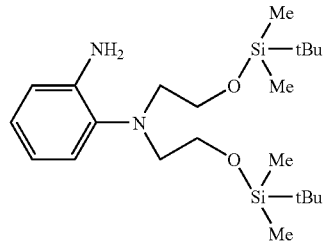

The title compound was prepared using 2-nitro-bis[2'-(tert-butyldimethyl silyloxy)ethyl]-aniline (X-4b) in a method analogous to that described in the previous Example. The product was purified by column chromatography (eluent: cyclohexane:AcOEt 3:1) and obtained as an oil (4.60 g, 99%).

$^1$H-NMR $\delta_H$ (ppm): 0.04 (s, 12H, Si—CH$_3$), 0.85 (s, 18H, Si-t-Bu), 3.02 (t, 4H, NCH$_2$, J=6.19 Hz), 3.56 (t, 4H, CH$_2$OSi), 6.49 (dt, 1H, H$_5$, J=7.51 Hz), 6.63 (dd, 1H, H$_3$, J=7.92 Hz), 6.78 (dt, 1H, H$_4$, J=7.54 Hz), 7.00 (dd, 1H, H$_6$, J=7.81 Hz); MS m/z: 425 (M$^+$+1, 28), 367 (M$^+$-t-Bu+1, 15); acc. mass: (C$_{22}$H$_{45}$N$_2$O$_2$Si$_2$) calcd. 425.3020, found 425.3034.

Example 7

4-(N'-Benzyloxycarbonyl-amino)-N,N-bis[(2'-(tert-butyldimethylsilyl-oxy)ethyl]-aniline (X-6a)

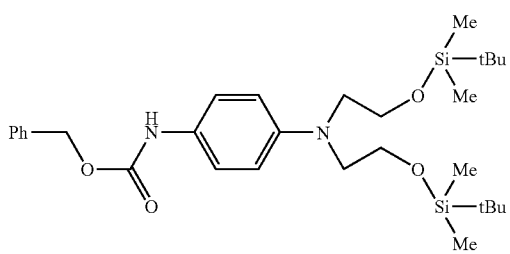

4-Amino-N,N-bis[(2'-(tert-butyldimethylsilyl-oxy)ethyl]-aniline (X-5a) (3.74 g, 8.8 mmol) was dissolved in THF (100 mL) and N-(benzyloxycarbonyloxy)-succinimide (2.25 g, 9.0 mmol) was added. The solution was stirred at room temperature for 16 h. The solvent was evaporated and the residue was purified by column chromatography (cyclohexane:ethyl acetate 1:1) to afford the title compound (4.65 g, 95%) as an oil.

$^1$H-NMR $\delta_H$ (ppm): −0.01 (s, 12H, SiCH$_3$), 0.84 (s, 18H, Si-t-Bu), 3.41 (t, 4H, NCH$_2$, J=5.86 Hz), 3.67 (t, 4H, CH$_2$OSi), 5.09 (s, 2H, PhCH$_2$), 6.58 (d, 2H, H$_{arom3+5}$, J=8.89 Hz), 6.82 (d, 2H, H$_{arom2+6}$), 7.28–7.40 (m, 5H, H$_{arom\,benzyl}$), 9.28 (s, 1H, NH). MS m/z: 558 (M$^+$, 35), 423 (M$^+$-PhCH$_2$—CO$_2$, 25); acc. mass: (C$_{30}$H$_{50}$N$_2$O$_4$Si$_2$) calcd. 558.3309, found 558.3330. Anal. (C$_{30}$H$_{50}$N$_2$O$_4$Si$_2$) C, H; N required 5.01, found 4.60%.

Example 8

4-(N'-Benzyloxycarbonyl-N'-methyl-amino)-N,N-bis[(2'-(tert-butyldimethylsilyi-oxy)ethyl]-aniline (X-7a)

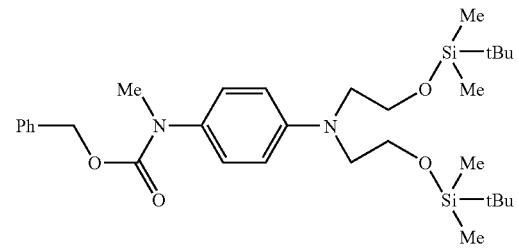

4-(N'-Benzyloxycarbonyl-amino)-N,N-bis[(2'-(tert-butyldimethylsilyl-oxy)ethyl]-aniline (X-6a) (5.2 g, 9.3 mmol) was dissolved in dry THF (60 mL) and NaH (60% in mineral oil, 0.6 g, 15 mmol) were added. After 40 min stirring at room temperature under argon, methyl iodide (586 μL, 9.3 mmol) was added and the stirring continued for 12 h. The solvent was evaporated, the residue redissolved in ethyl acetate (100 mL) and extracted with distilled water (100 mL). The organic layer was dried and evaporated to afford the title compound (5.34 g, 100%) as an oil.

$^1$H-NMR $\delta_H$ (ppm): 0.00 (s, 12H, Si—CH$_3$), 0.88 (s, 18H, Si-t-Bu), 3.21 (s, 3H, N—CH$_3$), 3.45 (t, 4H, NCH$_2$, J=6.47 Hz), 3.71 (t, 4H, CH$_2$OSi), 5.10 (s, 2H, PhCH$_2$), 6.60 (d, 2H, H$_{arom3+5}$, J=9.08 Hz), 6.99 (d, 2H, H$_{arom2+6}$, J=7.25 Hz), 7.20–7.35 (m, 5H, H$_{arom\,benzyl}$). MS m/z: 572 (M$^+$, 50), 595 (M$^+$+Na, 7), 437 (M$^+$-PhCH$_2$—CO$_2$, 45); acc. mass: (C$_{31}$H$_{52}$N$_2$O$_4$Si$_2$) calcd. 572.3466, found 572.3485.

Example 9

4-Methylamino-N,N-bis[(2'-(tert-butyldimethylsily-loxy)ethyl]-aniline (X-8a)

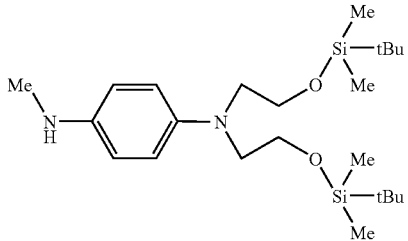

4-(N'-Benzyloxycarbonyl-N'-methyl-amino)-N,N-bis[(2'-(tert-butyldimethylsilyl-oxy)ethyl]-aniline (X-7a) (2.9 g, 5.06 mmol) was dissolved in ethyl acetate (120 mL), and Pd/C 10% catalyst (1.6 g) added. The suspension was stirred under $H_2$ atmosphere for 3 h. The catalyst was filtered off and the filtrate was evaporated to afford the title compound (2.23 g, 100%) as an oil.

$^1$H-NMR $\delta_H$ (ppm): −0.01 (s, 12H, $SiCH_3$), 0.84 (s, 18H, Si-t-Bu), 2.58 (s, 3H, N—$CH_3$), 3.22–3.32 (t, 4H, $NCH_2$), 3.63 (t, 4H, $CH_2OSi$, J=6.19 Hz), 4.87 (s, 1H, NH), 5.10 (s, 2H, $PhCH_2$), 6.43 (d, 2H, $H_{arom3+5}$, J=8.92 Hz), 6.65 (d, 2H, $H_{arom2+6}$), 7.20–7.35 (m, 5H, $H_{arom\ benzyl}$). MS m/z: 438 ($M^+$, 100), 451 ($M^+$+Na, 25); acc. mass: ($C_{23}H_{46}N_2O_2Si_2$) calcd. 438.3098, found 438.311500. Anal. ($C_{23}H_{46}N_2O_2Si_2$) C, H; N required 6.38, found 5.88.

Example 10

Diallyl L-glutamyl isocyanate (X-16)

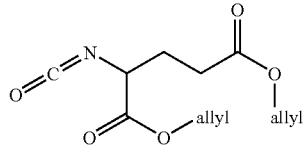

To diallyl L-glutamate p-toluene sulfonate (the TsOH salt of diallyl L-glutamate) (1.08 g, 2.7 mmol, NovaBiochem) and triphosgene (0.30 g, 1.03 mmol) in 20 mL toluene, stirred at −78° C., trietylamine (0.86 mL, 6.2 mmol) was added. After 30 min, the reaction mixture was allowed to reach room temperature and was used without further purification. A typical IR spectrum was obtained v=2253 cm$^{-1}$ (NCO, v. intense).

Example 11

Diallyl N-{(4-{hydroxymethyl}phenyl)carbamoyl]-L-glutamate (X-18)

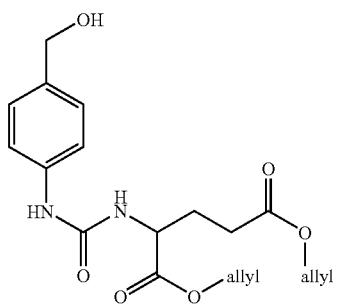

To a solution of diallyl glutamyl isocyanate (X-16) (25.0 mmol) in 100 mL of THF were added 4-aminobenzyl alcohol (X-9) (3.0 g, 24.3 mmol, Lancaster) and triethylamine (3.41 mL, 24.3 mmol) in 20 mL of THF, dropwise, over 10 min, at room temperature. The reaction was complete within 15 min. The reaction mixture was filtered and evaporated to dryness; the residue was dissolved in 20 mL of EtOAc, washed with water (2×20 mL), and dried ($MgSO_4$), before evaporating again. A yellow oil resulted (10.25 g); 2.7 g of the obtained product was submitted to purification by preparative HPLC ($CH_2Cl_2$:EtOAc, 1:1) which yielded 1.52 g (63%) of pure title compound.

$v_{max}$ cm$^{-1}$ (film) 8354 (NH—, OH, broad), 1737 (C=O, ester), 1659 (C=O, urea); $^1$H NMR $\delta_H$ 1.85–1.93 (m, 1H, $CH_2CH(NH)$—), 2.00–2.05 (m, 1H, —$CH_2CH(NH)$—), 2.46 (t, 2H, $CH_2CO_2$, J=5.4 Hz), 4.26–4.35 (m, 1H, —CH (NH)—), 4.40 (d, 2H, $CH_2$-Ph, J=5.6 Hz), 4.55 (d, 2H, $CH_2$O-allyl, J=5.3 Hz), 4.61 (d, 2H, $CH_2$O-allyl), 4.98 (t, 1H, OH), 5.17–5.37 (m, 4H, $CH_2$=allyl), 5.85–5.94 (m, 2H, CH=allyl), 6.56 (d, 1H, NH-G, J=8.0 Hz), 7.17 (d, 2, $H_{2+6}$, J=8.5 Hz), 7.32 (d, 2H, $H_{3+5}$), 8.52 (s, 1H, NH-Ph); MB m/z 399 ($M^+$+23, 35), 377 ($M^+$+1, 100), 359 ($M^+$-$H_2O$, 34). Anal. ($C_{19}H_{24}N_2O_6$) C, H, N.

Example 12

Diallyl N-(4-{[4-nitrophenoxycarbonyloxy] methyl}phenyl-carbamoyl)-L-glutamate (X-19)

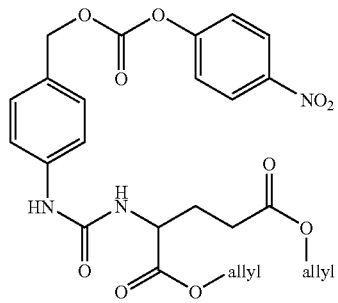

To a stirred solution of (X-18) (0.190 g, 0.50 mmol) in dry THF (10 mL) were added 4-nitrophenyl chloroformate (0.11 g, 0.5 mmol) and triethylamine (0.1 mL, 0.6 mmol) at room temperature. The reaction was complete after 1 h. The formed precipitate was filtered and the solution concentrated under vacuum. AcOEt (10 mL) was added; the solution was washed with brine (2×10 mL), dried ($MgSO_4$), and evaporated again, giving an oil which was purified by preparative HPLC to yield the title compound as a solid (0.132 g, 48.6%).

Mp 106–7° C.; $v_{max}$ cm$^{-1}$ (film) 3356 ($NH_2$), 2933 ($CH_2$), 1766 (C=0, carbonate), 1738 (C=O, ester), 1660 (C=O, amide), 1525, 1346 ($NO_2$). $^1$H NMR $\delta_H$ 1.86–1.95 (m, 1H, $CH_2CH(NH)$—), 2.00–2.05 (m, 1H, —$CH_2CH(NH)$—), 2.46 (t, 2H, $CH_2CO_2$, J=5.4 Hz), 4.28–4.33 (m, 1H, —CH (NH)—), 4.55 (d, 2H, $CH_2$O-allyl, J=5.3 Hz), 4.61 (d, 2H, $CH_2$O-allyl), 5.17–5.37 (m, 4H, $CH_2$=allyl), 5.22 (s, 2H, $CH_2$-Ph), 5.86–5.96 (m, 2H, CH=allyl), 6.65 (d, 1H, NH-G, J=8.3 Hz), 7.34 (d, 2H, $H_{3+5}$, J=8.7 Hz), 7.43 (d, 2H, $H_{2+6}$), 7.56 (d, 2H, $H_{3'+5'}$, J=9.1 Hz, 8.31 (d, 2H, $H_{2'+6'}$), 8.71 (s, 1H, NH-Ph)(G=glutamic moiety; Ph=phenyl); Mass ($C_{28}H_{27}N_3O_{10}Na$) calcd, 564.1594; found, 564.1590. Anal. ($C_{26}H_{27}N_3O_{10}$) H, N, C.

Example 13

Diallyl, 4-{N-[4'-bis(2"-tert-butyldimethylsilyloxy-ethyl)amino-phenyl]-N-methyl-carbamoyl-oxymethyl}-phenyl-carbamoyl-L-glutamate (X-20a)

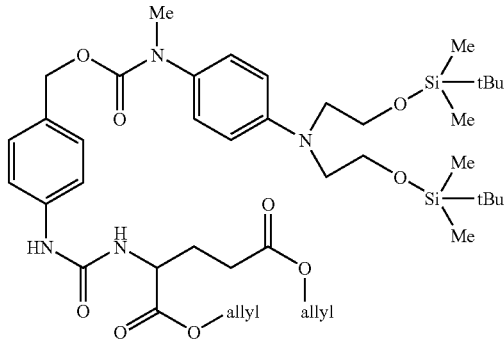

Diallyl N-(4-{[4-nitrophenoxycarbonyloxy]methyl}phenyl-carbamoyl)-L-glutamate (X-19) (2.1 g, 3.9 mmol) and 4-Methylamino-N,N-bis[(2'-(tert-butyldimethylsilyloxy)ethyl]-aniline (X-8a) (2.2 g, 5 mmol) were dissolved in DMA (50 mL) and stirred for 5 days at room temperature. The solvent was evaporated and the residue purified by column chromatography ($CH_2Cl_2$:AcOEt 9:1) to yield the title compound (0.92 g, 28%) as an oil.

$^1$H-NMR $\delta_H$ (ppm): 0.01 (s, 12H, Si—$CH_3$), 0.83 (s, 18H, Si-t-Bu), 1.80–2.10 (2m, 2H, $CH_2CH(NH)$—), 2.44 (t, 2H, $CH_2CO_2$, J=8.25 Hz), 3.11 (s, 3H, N—$CH_3$), 3.46 (t, 4H, $NCH_2$, J=5.58 Hz), 3.69 (t, 4H, $CH_2OSi$—), 4.25–4.35 (m, 1H, CH(NH)$CH_2$), 4.53 (d, 2H, $CH_2O$ allyl, J=5.45 Hz), 4.59 (d, 2H, $CH_2O$ allyl, J=6.38 Hz), 4.94 (s, 2H, $PhCH_2$), 5.14–5.38 (m, 4H, $CH_2$=allyl), 5.80–6.00 (m, 2H, CH=allyl), 6.60 (d, 3H, $H_{arom3'+5'}$=+NH-G, J=8.70 Hz), 6.99 (d, 2H, $H_{arom2'+6'}$), 7.15 (d, 2H, $H_{arom2+6}$), 7.32 (d, 2H, $H_{arom3+5}$, J=8.20 Hz), 8.60 (s, 1H, PhNH); MS m/z: 841 ($M^++1$, 5), 864 ($M^++Na$, 3), 437 ($M^+$-L1AC$H_2$OCO, 100); acc. mass: ($C_{43}H_{69}N_4O_9Si_2$) calcd. 841.4603, found 841.4630. Anal. ($C_{43}H_{68}N_4O_9Si_2$): C, H; N required 6.66, found 6.22.

Example 14

Diallyl, 4-{N-[4'-bis(2"-hydroxyethyl)amino-phenyl]-N-methyl-carbamoyl-oxymethyl}-phenyl-carbamoyl-L-glutamate (X-21a)

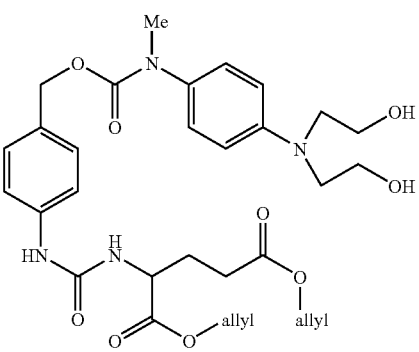

Diallyl, 4-{N-[4'-bis(2"-tert-butyldimethylsilyloxyethyl)amino-phenyl]-N-methyl-carbamoyl-oxymethyl}-phenyl-carbamoyl-L-glutamate (X-20a) (0.85 g, 1.0 mmol) was dissolved in 25 mL THF, 2.5 mL triethylamine trihydrofluoride were added and the solution stirred at room temperature for 7 h. The solvent was evaporated, the residue was diluted with AcOEt and extracted with $H_2O$ (100 mL), saturated aqueous $NaHCO_3$ (200 mL), again with $H_2O$ (100 mL), dried ($MgSO_4$) and evaporated to yield the title compound (0.58 g, 93.6%) as a gum.

$^1$H-NMR $\delta_H$ (ppm): 1.75–2.15 (2m, 2H, $CH_2CH(NH)$—), 2.44 (t, 2H, $CH_2CO_2$, J=8.54 Hz), 3.12 (s, 3H, N—$CH_3$), 3.38 (t, 4H, $NCH_2$, J=5.50 Hz), 3.50 (t, 4H, $CH_2OH$), 4.25–4.35 (m, 1H, CH(NH)$CH_2$), 4.53 (d, 2H, $CH_2O$ allyl, J=5.31 Hz), 4.59 (d, 2H, $CH_2O$ allyl, J=5.28 Hz), 4.71 (t, 2H, OH, J=5.45 Hz), 4.94 (s, 2H, $PhCH_2$), 5.15–5.38 (m, 4H, $CH_2$=allyl), 5.85–6.00 (m, 2H, CH=allyl), 6.61 (d, 3H, $H_{arom3'+5'}$+NH-G, J=8.90 Hz), 6.99 (d, 2H, $H_{arom2'+6'}$), 7.17 (d, 4H, $H_{arom2+6}$), 7.33 (d, 2H, $H_{arom3+5}$, J=8.09 Hz), 8.62 (s, 1H, PhNH); MS, m/z: 613 ($M^++1$, 45); acc. mass: ($C_{31}H_{41}N_4O_9$) calcd. 613.2874, found 613.2853. Anal. ($C_{31}H_{40}N_4O_9$): C, H, N.

Example 15

Diallyl, 4-{N-[4'-bis(2"-mesyloxyethyl)amino-phenyl]-N-methyl-carbamoyl-oxymethyl}-phenyl-carbamoyl-L-glutamate (X-22a)

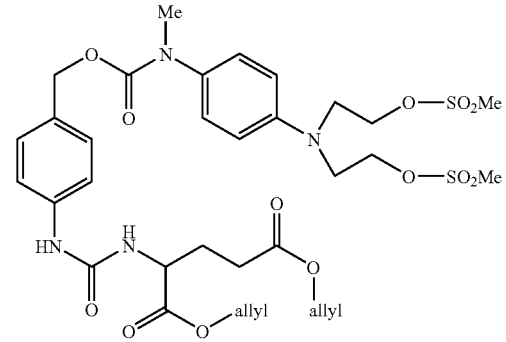

Over a solution of diallyl, 4-{N-[4'-bis(2"-hydroxyethyl)amino-phenyl]-N-methyl-carbamoyl-oxymethyl}-phenyl-carbamoyl-L-glutamate (X-21a) (0.58 g, 0.95 mmol), 4-N-dimethylaminopyridine (25 mg, 0.2 mmol) and $NEt_3$ (420 µL, 3.0 mmol) in $CH_2Cl_2$ (10 mL), mesyl anhydride (0.487 g, 2.8 mmol) dissolved in $CH_2Cl_2$ (15 mL) was added. After stirring at room temperature for 2.5 h, the solution was diluted with $CH_2Cl_2$ to 50 mL, extracted with 10% aq. citric acid (2×50 mL), aq. $NaHCO_3$ (50 mL), distilled water (50 mL), dried over $MgSO_4$ and evaporated to afford the title compound (0.73 g, 100%) as a gum.

$^1$H-NMR $\delta_H$ (ppm): 1.85–2.20 (2m, 2H, $CH_2CH(NH)$—), 2.44 (t, 2H, $CH_2CO_2$, J=7.77 Hz), 3.14 (s, 9H, $CH_3SO_3$, N—$CH_3$), 3.71 (t, 4H, $NCH_2$), 4.29 (t, 5H, $CH_2OMes$+CH(NH)$CH_2$, J=4.95 Hz), 4.54 (d, 2H, $CH_2O$ allyl, J=5.40 Hz), 4.60 (d, 2H, $CH_2O$ allyl, J=5.30 Hz), 4.96 (s, 2H, $PhCH_2$), 5.15–5.37 (m, 4H, $CH_2$=allyl), 5.80–6.00 (m, 2H, CH=allyl), 6.61 (d, 1H, NH-G, J=7.99 Hz), 6.75 (d, 2H, $H_{arom3'+5'}$, J=9.00 Hz), 7.08 (d, 2H, $H_{arom2'+6'}$), 7.18 (d, 2H, $H_{arom2+6}$) 7.33 (d, 2H, $H_{arom3+5}$, J=8.24 Hz), 8.61 (s, 1H, PhNH). MS m/z: 769 ($M^++1$, 4); acc. mass: ($C_{33}H_{45}N_4O_{13}S_2$) calcd. 769.2425, found 769.2456. Anal. ($C_{33}H_{44}N_4O_{13}S_2$): C, H, N, S.

Example 16

Diallyl, 4-{N-[4'-bis(2"-iodoethyl)amino-phenyl]-N-methyl-carbamoyl-oxymethyl}-phenyl-carbamoyl-L-glutamate (X-23a-I)

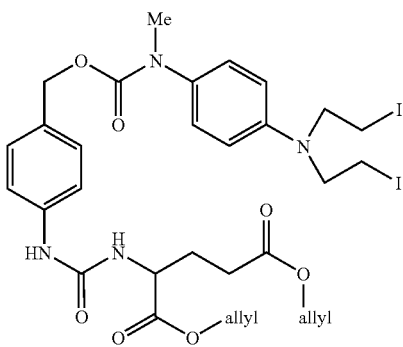

A solution of diallyl, 4-{N-[4'-bis(2"-mesyloxyethyl)amino-phenyl]-N-methyl-carbamoyl-oxymethyl}-phenyl-carbamoyl-L-glutamate (X-22a) (0.25 g, 0.33 mmol) and NaI (0.75 g, 5.0 mmol) in 25 mL acetone was stirred at reflux for 4 hrs. The solvent was evaporated, the residue retaken in 30 mL AcOEt and washed with 20 mL H$_2$O, dried (MgSO$_4$) and evaporated. The residue was purified by column chromatography (cyclohexane:AcOEt 1:1) to afford the title compound (0.165 g, 60%), as a solid, mp 138–140° C.

$^1$H-NMR δ$_H$ (ppm): 1.80–2.15 (2m, 2H, CH$_2$CH(NH)—), 2.44 (t, 2H, CH$_2$CO$_2$), 3.13 (s, 3H, N—CH$_3$), 3.25–3.35 (t, 4H, NCH$_2$), 3.70 (t, 4H, CH$_2$I, J=6.17 Hz), 4.25–4.40 (m, 1H, CH(NH)CH$_2$), 4.54 (d, 2H, CH$_2$O allyl, J=6.27 Hz), 4.60 (d, 2H, CH$_2$O allyl, J=4.42 Hz), 4.95 (s, 2H, PhCH$_2$), 5.10–5.37 (m, 4H, CH$_2$=allyl), 5.80–6.00 (m, 2H, CH=allyl), 6.62 (d, 3H, H$_{arom3'+5'}$+NH-G, J=8.67 Hz), 7.09 (d, 2H, H$_{arom2'+6'}$), 7.18 (d, 2H, H$_{arom2+6}$), 7.33 (d, 2H, H$_{arom3+5}$, J=7.72 Hz), 8.61 (s, 1H, PhNH). MS m/z: 833 (M$^+$+1, 7), 855 (M$^+$+Na, 14); acc. mass: (C$_{31}$H$_{38}$N$_4$O$_7$I$_2$Na) calcd. 855.0728, found 855.0755. Anal. (C$_{31}$H$_{38}$N$_4$O$_7$I$_2$): H, N; C required 44.73, found 45.24%.

Example 17

Diallyl, 4-{N-[4'-bis(2"-bromoethyl)amino-phenyl]-N-methyl-carbamoyl-oxymethyl}-phenyl-carbamoyl-L-glutamate (X-23a-Br)

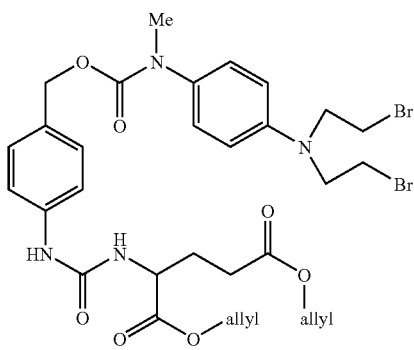

To a THF solution (25 mL) of diallyl, 4-{N-[4'-bis(2"-mesyloxyethyl)amino-phenyl]-N-methyl-carbamoyl-oxymethyl}-phenyl-carbamoyl-L-glutamate (X-22a) (0.26 g, 0.34 mmol), LiBr (0.44 g, 5.0 mmol) was added. After 1.5 h stirring at reflux the solvent was evaporated, the residue retaken in CH$_2$Cl$_2$ (25 mL), extracted with H$_2$O (25 mL), the organic layer dried (MgSO$_4$) and evaporated to dryness. Purification was achieved by preparative HPLC (cyclohexane:AcOEt 3:1), and the title compound (0.16 g, 64%) was obtained as a solid, mp 104–107° C.

$^1$H-NMR δ$_H$ (ppm): 1.80–2.15 (2m, 2H, CH$_2$CH(NH)—), 2.44 (t, 2H, CH$_2$CO$_2$), 3.13 (s, 3H, N—CH$_3$), 3.56 (t, 4H, NCH$_2$, J=6.74 Hz), 3.75 (t, 4H, CH$_2$Br), 4.25–4.35 (m, 1H, CH(NH)CH$_2$), 4.54 (d, 2H, CH$_2$O allyl, J=5.52 Hz), 4.59 (d, 2H, CH$_2$O allyl, J=5.21 Hz), 4.95 (s, 2H, PhCH$_2$), 5.10–5.37 (m, 4H, CH$_2$=allyl), 5.80–6.00 (m, 2H, CH=allyl), 6.61 (d, 1H, NH-G, J=8.34 Hz), 6.68 (d, 2H, H$_{arom3'+5'}$, J=8.89 Hz), 7.09 (d, 2H, H$_{arom2'+6'}$), 7.18 (d, 2H, H$_{arom2+6}$), 7.33 (d, 2H, H$_{arom3+5}$, J=8.26 Hz), 8.61 (s, 1H, PhNH). MS m/z: 738 (M$^+$, 5), 761 (M$^+$+Na, 15); acc. mass: (C$_{31}$H$_{38}$N$_4$O$_7$Br$_2$) calcd. 759.1005, found 759.1021. Anal. (C$_{31}$H$_{38}$N$_4$O$_7$Br$_2$): C, H, N.

Example 18

Diallyl, 4-{N-[4'-bis(2"-chloroethyl)amino-phenyl]-N-methyl-carbamoyl-oxymethyl}-phenyl-carbamoyl-L-glutamate (X-23a-Cl)

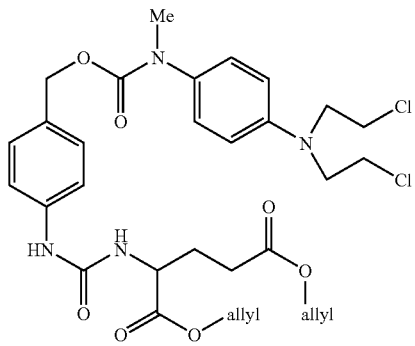

Diallyl, 4-{N-[4'-bis(2"-mesyloxyethyl)amino-phenyl]-methyl-carbamoyl-oxymethyl}-phenyl-carbamoyl-L-glutamate (X-22a) (0.245 g, 0.32 mmol) was dissolved in DMA (25 mL). Lithium chloride (0.21 g, 5 mmol) was added to the reaction mixture and it was stirred for 24 h at room temperature. The solvent was evaporated, the residue taken in AcOEt (50 mL) and extracted with distilled water (2×50 mL). The organic layer was separated, dried (MgSO$_4$) and evaporated. The residue was purified by column chromatography (eluent AcOEt:cyclohexane 1:1) to afford the title compound (0.105 g, 51%) as a gum.

$^1$H-NMR δ$_H$ (ppm): 1.80–2.20 (2m, 2H, CH$_2$CH(NH)—), 2.44 (t, 2H, CH$_2$CO$_2$, J=8.26 Hz), 3.13 (s, 3H, N—CH$_3$), 3.70 (s, 8H, N(CH$_2$CH$_2$Cl)$_2$), 4.25–4.40 (m, 1H, CH(NH)CH$_2$), 4.54 (d, 2H, CH$_2$O allyl, J=5.44 Hz), 4.59 (d, 2H, CH$_2$O allyl, J=5.35 Hz), 4.95 (s, 2H, PhCH$_2$), 5.10–5.35 (m, 4H, CH$_2$=allyl), 5.80–6.00 (m, 2H, CH=allyl), 6.61 (d, 1H, NH-G, J=8.35 Hz), 6.70 (d, 2H, H$_{arom3'+5'}$, J=8.86 Hz), 7.08 (d, 2H, H$_{arom2'+6'}$), 7.18 (d, 2H, H$_{arom2+6}$), 7.33 (d, 2H, H$_{arom3+5}$, J=8.56 Hz), 8.61 (s, 1H, PhNH). MS m/z: 671 (M$^+$+Na, 20); acc. mass: (C$_{31}$H$_{38}$N$_4$O$_7$Cl$_2$Na) calcd. 671.2015, found 671.2037. Anal. (C$_{31}$H$_{38}$N$_4$O$_7$Cl$_2$): C, H, N Cl.

Example 19

4-{N-[4'-bis(2"-iodoethyl)amino-phenyl]-N-methyl-carbamoyl-oxymethyl}-phenyl-carbamoyl-L-glutamic acid (X-24a-I) (P-1)

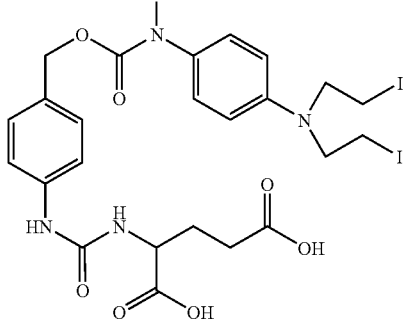

Diallyl, 4-{N-[4'-bis(2"-iodoethyl)amino-phenyl]-N-methyl-carbamoyl-oxymethyl}-phenyl-carbamoyl-L-glutamate (X-23a-I) (0.145 g, 0.17 mmol) and Pd tetrakistriphenylphosphine (15 mg, 15 μmol) were dissolved in 4 mL CH$_2$Cl$_2$. Pyrrolidine (58 μL, 0.70 mmol) was added in one portion. After 30 min stirring, the solution was diluted with AcOEt. The pyrrolidine salt of the deprotected carboxylic acid precipitated at once. The reaction mixture was partially evaporated, the remaining solvent was diluted with AcOEt and concentrated to remove CH$_2$Cl$_2$ selectively. The precipitate left in the flask after discarding the solvent was washed twice with AcOEt, dried, dissolved in 8 mL methanol and eluted through a column loaded with 40 cm$^3$ IRC50 resin (H form) previously washed with MeOH. After evaporation the elute yield the title compound as a solid (0.105 g, 77.8%), mp 103–105° C.

$^1$H-NMR δ$_H$ (ppm): 1.75–2.00 (2m, 2H, CH$_2$CH(NH)—), 2.28 (t, 2H, CH$_2$CO$_2$, J=7.43 Hz), 3.14 (s, 3H, N—CH$_3$), 3.30 (t, 4H, NCH$_2$), 3.72 (t, 4H, CH$_2$I, J=7.64 Hz), 4.10–4.25 (m, 1H, CH(NH)CH$_2$), 4.96 (s, 2H, PhCH$_2$), 6.46 (d, 1H, NH-G, J=7.48 Hz), 6.64 (d, 2H, H$_{arom3'+5'}$, J=8.85 Hz), 7.10 (d, 2H, H$_{arom2'+6'}$), 7.17 (d, 2H, H$_{arom2+6}$, J=7.49 Hz), 7.34 (d, 2H, H$_{arom3+5}$), 8.68 (s, 1H, PhNH). MS m/z: 752 (M$^+$+1, 10), 775 (M$^+$+Na, 35); acc. mass: (C$_{25}$H$_{30}$N$_4$O$_7$I$_2$Na) calcd. 775.0102, found 775.0088.

Example 20

4-{N-[4'-bis(2"-bromoethyl)amino-phenyl]-N-methyl-carbamoyl-oxymethyl}-phenyl-carbamoyl-L-glutamic acid (X-24a-Br) (P-2)

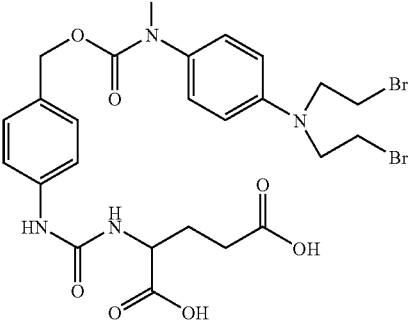

The title compound was prepared from diallyl, 4-{N-[4'-bis(2"-bromoethyl)amino-phenyl]-N-methyl-carbamoyl-oxymethyl}-phenyl-carbamoyl-L-glutamate (X-23a-Br) by a method analogous to that described in the previous Example (0.10 g, 80%), mp 75–77° C.

$^1$H-NMR δ$_H$ (ppm): 1.80–1.95 (m, 2H, CH$_2$CH(NH)—), 2.28 (t, 2H, CH$_2$CO$_2$, J=7.33 Hz), 3.14 (s, 3H, N—CH$_3$), 3.71 (s, 8H, N(CH$_2$CH$_2$Cl)$_2$), 4.10–4.20 (m, 1H, CH(NH)CH$_2$), 4.95 (s, 2H, PhCH$_2$), 6.48 (d, 1H, NH-G, J=7.17 Hz), 6.68 (d, 2H, H$_{arom3'+5'}$, J=8.74 Hz), 7.09 (d, 2H, H$_{arom2'+6'}$), 7.18 (d, 2H, H$_{arom2+6}$), 7.34 (d, 2H, H$_{arom\ 3+5}$, J=8.45 Hz), 8.74 (s, 1H, PhNH). MS m/z: 658 (M$^+$, 8), 681 (M$^+$+Na, 15); acc. mass: (C$_{25}$H$_{30}$N$_4$O$_7$Br$_2$Na) calcd. 679.0379, found 679.0386.

Example 21

4-{N-[4'-bis(2"-chloroethyl)amino-phenyl]-N-methyl-carbamoyl-oxymethyl}-phenyl-carbamoyl-L-glutamic acid (X-24a-Cl) (P-3)

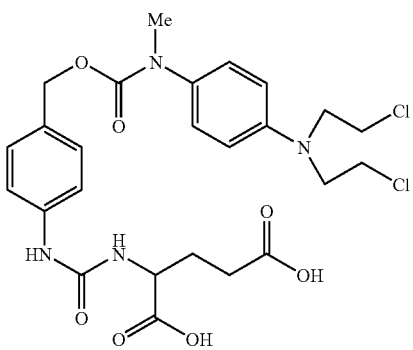

The title compound was prepared from diallyl, 4-{N-[4'-bis(2"-chloroethyl)amino-phenyl]-N-methyl-carbamoyl-oxymethyl}-phenyl-carbamoyl-L-glutamate (X-23a-Cl) by a method analogous to that described in the previous Example (0.075 g, 90%), mp 70–72° C.

$^1$H-NMR δ$_H$ (ppm): 1.75–2.00 (2m, 2H, CH$_2$CH(NH)—), 2.27 (t, 2H, CH$_2$CO$_2$), 3.14 (s, 3H, N—CH$_3$), 3.71 (s, 8H, N(CH$_2$CH$_2$Cl)$_2$), 4.10–4.20 (m, 1H, CH(NH)CH$_2$), 4.95 (s, 2H, PhCH$_2$), 6.49 (d, 1H, NH-G), 6.70 (d, 2H, H$_{arom3'+5'}$, J=8.60 Hz), 7.09 (d, 2H, H$_{arom2'+6'}$), 7.18 (d, 2H, H$_{arom2+6}$), 7.34 (d, 2H, H$_{arom3+5}$, J=8.14 Hz), 8.71 (s, 1H, PhNH). MS m/z: 568 (M$^+$, 25), 591 (M$^+$+Na, 100); acc. mass: (C$_{25}$H$_{30}$N$_4$O$_7$Cl$_2$Na) calcd. 591.1389, found 591.1371.

Biological Data

Cytotoxicity Assays

Prodrugs of the invention (P), comparison prodrugs (CP), and some of the corresponding drugs (D) were tested for cytotoxicity in WiDr cells (a colon carcinoma cell line) engineered for stable expression of (stCPG2(Q)3) or, as a control, the non-prodrug activating enzyme β-galactosidase (β-gal). The construction of WiDr cells engineered to stably express stCPG2(Q)3 or β-gal, was performed as previously described for other cell lines (see Marais et al., 1997; Niculescu-Duvaz et al., 1998b).

Cells (2×10$^6$) were seeded into 6-well plates, producing confluent monolayers in 48 hrs. Compounds were dissolved in DMSO at 10 mM (CP-2, CP-4, CP-9, CP-11), 20 mM (D-1, D-3, D-5, D-6), or 50 mM (all others), immediately prior to treatment, diluted in culture medium, and added to the wells. A similar concentration of compound solution was added after an incubation of 1 hour, and the cells were incubated for an additional 20 hrs. The cells were harvested and re-seeded in quadruplicate in 96-well plates at ~2×10$^3$/well and incubated until the control wells achieved confluence. The plates were then fixed and stained with sulforhodamine-B, the extinction at 590 nm was determined, and the results expressed as percentage of control growth as a function of log(dose). The IC$_{50}$ was determined by non-linear regression to a log dose-effect sigmoid, constraining the minimum to be positive (using GraphPad Prism®, GraphPad Software Inc., San Diego, Calif., USA).

For comparison purposes, the prodrug N-{4-[(2-chloroethyl)(2-mesyloxyethyl)amino]benzoyl}-L-glutamic acid prodrug (CMDA, see below), which has undergone clinical trials in ADEPT (see Martin et al., 1997; Napier et al., 2000), was also tested.

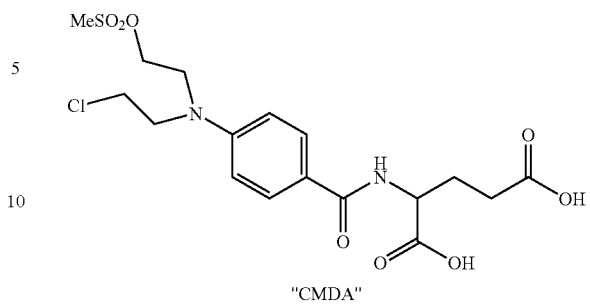

"CMDA"

The degree of activation is defined as the ratio of the IC$_{50}$ value of the prodrug in the β-gal expressing cell line to the IC$_{50}$ value of the prodrug in CPG2 expressing cell line.

The results are summarised in the following tables, wherein the prodrugs and drugs have the following formulae:

TABLE 1

Cytotoxicity Data (Prodrugs)

| Cmpd. | Z | o/p | R$^N$ | X$^1$ | X$^2$ | IC$_{50}$(μM) LacZ | IC$_{50}$(μM) stCPG2(Q)3 | Degree of activation (fold) |
|---|---|---|---|---|---|---|---|---|
| CMDA | n/a | para | H | Cl | Cl | 3230 [±120] | 100 [±10] | 32.3 |
| CP-1 | NH | ortho | H | I | I | 149.0 (80.7–275.0) | 3.0 (2.1–4.4) | 49.7 |
| CP-2 | NH | para | H | I | I | 179.8 (71.7–449.4) | 1.8 (1.0–3.2) | 101.6 |
| CP-3 | NH | ortho | H | Br | Br | 117.7 (83.8–165.2) | 4.7 (7.8–27.8) | 24.9 |
| CP-4 | NH | para | H | Br | Br | 204.6 (108.6–384.6) | 3.1 (1.8–5.3) | 66.6 |
| CP-5 | NH | ortho | H | Cl | Cl | 21.1 (12.0–36.9) | 4.5 (2.9–7.1) | 4.7 |
| CP-6 | NH | para | H | Cl | Cl | — | — | — |
| CP-7 | O | ortho | H | OMes | OMes | 208.2 (86.4–500.7) | 40.0 (22.7–70.3) | 5.2 |
| CP-8 | O | ortho | H | I | I | 73.3 (45.3–119.8) | 19.0 (11.7–30.9) | 3.9 |
| CP-9 | O | para | H | I | I | 53.6 (36.9–78.0) | 1.3 (0.8–2.0) | 42.5 |

TABLE 1-continued

Cytotoxicity Data (Prodrugs)

prodrugs drugs

| Cmpd. | Z | o/p | $R^N$ | $X^1$ | $X^2$ | IC$_{50}$(μM) LacZ | IC$_{50}$(μM) stCPG2(Q)3 | Degree of activation (fold) |
|---|---|---|---|---|---|---|---|---|
| CP-10 | O | ortho | H | Br | Br | 183.4 (83.8–400.4) | 95.2 (57.1–159) | 1.9 |
| CP-11 | O | para | H | Br | Br | 99.7 (19.1–520.6) | 2.6 (1.2–6.0) | 38.3 |
| CP-12 | O | ortho | H | Cl | Cl | 38.1 (19.1–76) | 28.1 (11.1–43.6) | 1.4 |
| CP-13 | O | para | H | Cl | Cl | — | — | — |
| CP-14 | O | ortho | H | OMes | Cl | 148.4 (65.1–338.2) | 28.5 (17.5–47.5) | 5.2 |
| CP-15 | O | para | Me | I | I | 21.5 (16.2–28.4) | 2.6 (1.7–4.1) | 8.3 |
| CP-16 | O | para | Me | Br | Br | 27.2 (14.1–52.5) | 3.6 (2.2–6.0) | 7.5 |
| CP-17 | O | para | Me | Cl | Cl | 19.6 (15.0–25.7) | 1.7 (1.1–2.5) | 11.5 |
| P-1 | NH | para | Me | I | I | 184.7 (105.4–324.4) | 1.5 (0.8–2.6) | 124.0 |
| P-2 | NH | para | Me | Br | Br | 332.4 (222.6–496.3) | 4.1 (2.5–6.7) | 81.4 |
| P-3 | NH | para | Me | Cl | Cl | 39.7 (27.0–58.4) | 2.5 (1.6–3.9) | 15.9 |

Note:
the round ( ) bracketed values indicate the 95% confidence intervals.

Note:
For CMDA, the square [ ] bracketed values represent the standard errors of the mean as published in Spooner et al., 2000.

TABLE 2

Cytotoxicity Data (Drugs)

| Cmpd. no | o/p | $R^N$ | $X^1$ | $X^2$ | IC$_{50}$(μM) LacZ | IC$_{50}$(μM) stCPG2(Q)3 | Degree of activation (fold) |
|---|---|---|---|---|---|---|---|
| D-1 | para | H | I | I | 10.2 (4.8–18.3) | 8.6 (4.2–14.0) | 1.2 |
| D-2 | ortho | H | Br | Br | 23.4 (12.4–44.1) | 18.6 (10.7–32.2) | 1.3 |
| D-3 | para | H | Br | Br | 9.4 (5.7–18.5) | 7.7 (5.0–14.8) | 1.2 |
| D-4 | ortho | H | Cl | Cl | 3.5 (2.1–5.7) | 2.4 (1.3–4.4) | 1.5 |
| D-5 | para | Me | I | I | 7.7 (4.1–14.5) | 8.4 (4.6–15.5) | 0.92 |
| D-6 | para | Me | Br | Br | 7.2 (3.6–14.4) | 7.4 (3.5–15.5) | 0.97 |

TABLE 2-continued

Cytotoxicity Data (Drugs)

| Cmpd. no | o/p | $R^N$ | $X^1$ | $X^2$ | IC$_{50}$(μM) LacZ | IC$_{50}$(μM) stCPG2(Q)3 | Degree of activation (fold) |
|---|---|---|---|---|---|---|---|
| D-7 | para | Me | Cl | Cl | 9.2 (5.7–15.1) | 8.2 (5.3–12.5) | 1.1 |

Note:
the bracketed ( ) values indicate the 95% confidence intervals.

The differential obtained in tumor cells transfected with CPG2 appears to be dependent upon an optimal chemical reactivity of the prodrugs and the corresponding drugs. This is in good agreement with previous observation on the in vitro and in vivo behaviour of the direct prodrugs in CPG2-based GDEPT systems (see Friedlos et al., 2002). The increased lipophilicity of these prodrugs and drugs could also be important for their improved biological activity.

The inventors postulate that N-alkylation (e.g., N-methylation) of the prodrug results in (a) improved stability of the carbamate linkage between the linker and the drug moiety, and (b) increased basicity, and therefore increased chemical reactivity, of the released nitrogen mustard drug.

N-alkylation (e.g., N-methylation) has a beneficial effect on their biological activity despite no observed benefit to the kinetics. The prodrugs show lower chemical reactivity than the non-methylated counterparts, presumably due to increased stability of the secondary carbamate. This effect is minimal at the drug level.

As a general observation, prodrugs incorporating ureas (Z=NH) are more effective than those containing carbamates (Z=O). The five most effective prodrugs, in terms of differential, are all ureas (Z=NH).

The use of I and Br instead of Cl as leaving groups in the nitrogen mustards leads to drugs with shorter half-lives and increased potency (IC$_{50}$=0.5–2.7 μM). The corresponding prodrugs also exhibited shorter half-lives. Nonetheless, for many of the prodrugs the differentials in the WiDr cell lines are better than those of CMDA (CP-1, CP-2, CP-4, CP-9, CP-11, P-1, P-2). The two most effective prodrugs in terms of differential are the iodo derivatives CP-2 and P-1. The most effective prodrug in terms of differential is the N-methylated iodo derivative P-1.

The prodrugs belonging to the ortho series are less effective than their para counterparts. However, even in the ortho series, the I and Br nitrogen mustard prodrugs are the most active and significant differentials were obtained in the transfected WiDr cell line (50 and 25 fold for CP-1 and CP-3 respectively). The ortho prodrugs had lower K$_m$'s with respect to the linkers and the para series, which is of potential benefit in in vivo situations.

Aqueous Half-Life Determination

The chemical half-lives of the prodrugs and some of the corresponding drugs were determined by HPLC or a spectrophotometric method.

Compounds were prepared as 10 mM concentrates in MeOH (D-2, D-4) or in DMSO (all others) and diluted 100 fold in CPG2 assay buffer (100 mM Tris-HCl, pH 7.3; 260 μM ZnCl$_2$; 1 mL) to give 100 μM solutions. Aliquots (10 μL) were injected into a Partisphere C18 column (125×4.6 mm, 5 μm, Whatman) (compounds D4, D-7) or a Synergi Polar RP phenyl phase column (150×4.6 mm, 4 μm, Phenomenex) (all others) and eluted isocratically (1 mL/min) with 10 mM ammonium acetate (pH 5.0) containing percentages of methanol (65–85%) that gave retention times of 3–4 minutes. The eluate was monitored at 265–275 nm (CP-9, CP-11, CP-15, CP-16, CP-17) or 250 nm (all others). The amount of starting material remaining after various periods of incubation was determined either by repeat injection from a single vial (CP-5, CP-12, CP-15, CP-17, P-1, P-3), or by delayed injections from a new vial each time (all others). The results were expressed as fraction of starting material as a function of time, and the half-life determined by non-linear regression to a one-phase exponential decay, constraining the maximum to 1 and the minimum to 0 (GraphPad Prism®).

Compounds D-1, D-2, D-3, D-5 and D-6 proved too labile for half-life determination by HPLC, and a spectrophotometric method was employed. The change in absorbance on dilution into aqueous conditions at a wavelength previously determined to give the largest difference was monitored for 3 min at a sampling rate of 100/min. The data were fitted to a rising or falling exponential by linear regression with no constraints (GraphPad Prism®), and the half life calculated as 0.69/rate constant. It was established that this method gave similar results to the more unequivocal HPLC method.

The results are summarised in the following tables.

TABLE 3

Aqueous Half Lives (Prodrugs)

| Comp No. | Z | o/p | $R^N$ | $X^1$ | $X^2$ | T1/2 prodrug (min) | T1/2 prodrug/ T1/2 drug |
|---|---|---|---|---|---|---|---|
| CP-1 | NH | ortho | H | I | I | 2.7 | — |
| CP-2 | NH | para | H | I | I | 0.97 | 1.9 |
| CP-3 | NH | ortho | H | Br | Br | 3.0 | 3.5 |
| CP-4 | NH | para | H | Br | Br | 0.85 | 0.4 |
| CP-5 | NH | ortho | H | Cl | Cl | 107.5 | 13.9 |
| CP-6 | NH | para | H | Cl | Cl | | |
| CP-7 | O | ortho | H | OMes | OMes | 10.8 | — |
| CP-8 | O | ortho | H | I | I | 2.1 | — |
| CP-9 | O | para | H | I | I | 0.98 | 2.0 |
| CP-10 | O | ortho | H | Br | Br | 3.47 | 3.5 |
| CP-11 | O | para | H | Br | Br | 0.9 | 0.4 |
| CP-12 | O | ortho | H | Cl | Cl | 146.3 | 11.9 |
| CP-13 | O | para | H | Cl | Cl | | |
| CP-14 | O | ortho | H | OMes | Cl | 10.0 | — |
| CP-15 | O | para | Me | I | I | 4.6 | 7.7 |
| CP-16 | O | para | Me | Br | Br | 2.7 | 1.0 |
| CP-17 | O | para | Me | Cl | Cl | 173.6 | 20.6 |
| P-1 | NH | para | Me | I | I | 3.9 | 6.5 |
| P-2 | NH | para | Me | Br | Br | 2.8 | 1.0 |
| P-3 | NH | para | Me | Cl | Cl | 173.6 | 20.9 |

TABLE 4

Aqueous Half-lives (Drugs)

| Compd. no | o/p | $R^N$ | $X^1$ | $X^2$ | T1/2 (min) |
|---|---|---|---|---|---|
| D-1 | para | H | I | I | 0.5 |
| D-2 | ortho | H | Br | Br | 1.0 |
| D-3 | para | H | Br | Br | 2.3 |
| D-4 | ortho | H | Cl | Cl | 12.3 |
| D-5 | para | Me | I | I | 0.6 |
| D-6 | para | Me | Br | Br | 2.7 |
| D-7 | para | Me | Cl | Cl | 8.3 |

Difficulties were encountered in determining the half-lives of the ortho nitrogen mustards. All the ortho nitrogen mustard drugs (D-1, D-2, and D-4) have the correct microanalysis. However $^1$H-NMR (in DMSO-d$_6$) and LC- MS (in DMSO-buffer) showed rapid cyclisation to the corresponding benzopiperidine derivative (as shown below), except for the bis(chloroethyl) derivative D-4.

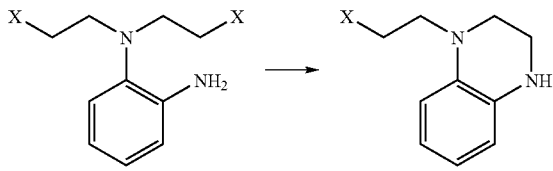

Comparisons based upon 4-amino ($R^N$=H) versus 4-methylamino ($R^N$=Me), and 4-amino (para) versus 2-amino (ortho) are summarised in the following tables.

TABLE 5

Comparison of Half-Lives:
4-amino ($R^N$ = H) versus 4-methylamino ($R^N$ = Me)

| Comps. | Z | o/p | $X^1$ | $X^2$ | $T_{1/2}$ ratio |
|---|---|---|---|---|---|
| CP-6/P-3 | NH | para | Cl | Cl | 0.28 |
| CP-4/P-2 | NH | para | Br | Br | 0.30 |
| CP-2/P-1 | NH | para | I | I | 0.25 |
| CP-13/CP-15 | O | para | Cl | Cl | 0.30 |
| CP-10/CP-14 | O | para | Br | Br | 0.33 |
| CP-8/CP-13 | O | para | I | I | 0.21 |

TABLE 6

Comparison of Half-Lives:
4-amino (para) versus 2-amino (ortho)

| Comps. | Z | $R^N$ | $X^1$ | $X^2$ | $T_{1/2}$ ratio |
|---|---|---|---|---|---|
| CP-6/CP-5 | NH | H | Cl | Cl | 0.45 |
| CP-4/CP-3 | NH | H | Br | Br | 0.28 |
| CP-2/CP-1 | NH | H | I | I | 0.36 |
| CP-13/CP-12 | O | H | Cl | Cl | 0.35 |
| CP-11/CP-10 | O | H | Br | Br | 0.26 |
| CP-9/CP-8 | O | H | I | I | 0.47 |

In general, the 4-amino aniline mustard prodrugs have shorter half lives than the N-methylated and their 2-amino counterparts.

The half-lives of the N-methylated prodrugs are consistently 3–4 times longer than the corresponding non-methylated prodrugs, irrespective of the halogen in the mustard moiety or the type of linker (Z=NH or Z=O).

Similarly the ortho amino analogues have half-lives 2–3 times longer than para amino prodrugs.

Enzyme Kinetics

The kinetics of activation of the self-immolative prodrugs by CPG2 was measured for the bis(chloroethyl) series. This series was chosen in order to minimise the influence of the nitrogen mustard moiety hydrolysis on the measured kinetics.

Reactions were set up containing CPG2 assay buffer (1 mL), CPG2 (50 mU) and prodrug (5–50 µM in steps of 5 µM) from concentrates as above. The vials were incubated at 37° C., and the amount of prodrug remaining in the mixture was determined by HPLC as above at 0, 5, 10, 15 and 20 minutes post start. The rate of loss of compound in µM/min was determined by regression. The rate of chemical-only loss, calculated from the first derivative of the equation for exponential decay, was substracted, and the kinetic parameters derived from non-linear regression to the Michaelis-Menten equation (GraphPad Prism®).

The results are summarised in the following table.

TABLE 7

Kinetics Results

| Compd. no | Z | o/p | $R^N$ | $X^1$ | $X^2$ | $K_m$ (µM) | $k_{cat}$ ($s^{-1}$) | $K_{cat}/K_m$ |
|---|---|---|---|---|---|---|---|---|
| L1-OH[(a)] | NH | n/a | n/a | n/a | n/a | 3.1 | 65.4 | 21.1 |
| L2-OH[(b)] | O | n/a | n/a | n/a | n/a | 1.7 | 140 | 82.3 |
| CP-5 | NH | ortho | H | Cl | Cl | 0.55 | 2.92 | 5.31 |
| CP-6 | NH | para | H | Cl | Cl | <5 | 10–50 | — |
| CP-12 | O | ortho | H | Cl | Cl | 1.03 | 4.27 | 4.14 |
| CP-13 | O | para | H | Cl | Cl | <5 | <10 | — |
| CP-17 | O | para | Me | Cl | Cl | 2.43 | 4.32 | 1.78 |
| P-3 | NH | para | Me | Cl | Cl | 6.05 | 5.50 | 0.91 |

Two analogs, (a) and (b), were included for comparison purposes. They are:

(c) L1-OH=N-[4-(hydroxymethyl)phenyl-carbamoyl]-L-glutamatic acid.

(d) L2-OH=N-[4-(hydroxymethyl)phenyl-oxycarbonyl]-L-glutamatic acid.

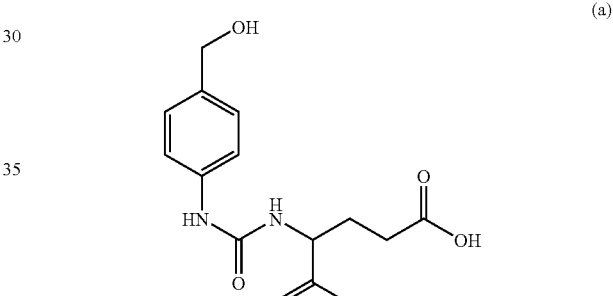

(a)

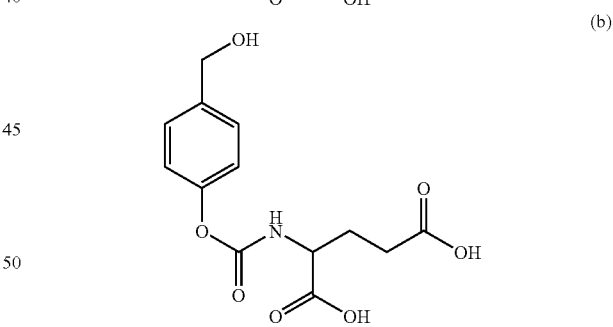

(b)

All prodrugs showed $K_m$'s comparable with those of L1-OH (Z=NH) and L2-OH (Z=O) (see Niculescu-Duvaz et al., 1998b). This indicates a good structural fit for the CPG2 active site, even with the ortho derivatives. However, the $k_{cat}$ remains low compared to the direct prodrugs and the linkers alone.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined by the appended claims.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Bagshawe et al., 1988, "A Cytotoxic Agent Can Be Generated Selectively At Cancer Sites," *British Journal of Cancer*, Vol. 58, p. 700.

Bagshawe et al., 1994, "Antibody-Directed Enzyme Prodrug Therapy (ADPET): A Review of Some Theoretical, Experimental and Clinical Aspects," *Analytical Oncology*, Vol. 5, p. 879.

Denny and Wilson, 1998, "The Design of Selectively-Activated Anti-Cancer Prodrugs for Use in Antibody-Directed and Gene-Directed Enzyme Prodrug Therapies," *Journal of Pharmaceutical Pharmacology*, Vol. 50, p. 387.

Deonarain and Epenetos, 1994, "Targeting Enzymes for Cancer Therapy: Old Enzymes in New Roles," *British Journal of Cancer*, Vol. 70, p. 786.

Dowell et al., 1996, "New Mustard Prodrugs for Antibody-Directed Enzyme Prodrug Therapy: Alternative for the Amide Link," *Journal of Medicinal Chemistry*, Vol. 39, p. 1100.

Encell and Loeb, 1998, "Improving Enzymes for Cancer Gene Therapy," *Tumor Targeting*, Vol. 3, p. 191.

Ferenz, C. R., et al., 1989, *Journal of Labelled Compounds & Radiopharmaceuticals*, Vol. 27, pp. 737–751.

Friedlos, F.; Davies, L.; Scanlon, I.; Ogilvie, L. M.; Martin, J.; Stribbling, S. M.; Niculescu-Duvaz, I.; Marais, R.; Springer, C. J., 2002, "Three new prodrugs for suicide gene therapy using CPG2 all elicit improved bystander effect efficacy in two xenograft models," *Cancer Research*, Vol. 62, pp. 1724–1729.

Hay and Denny, 1996, "Antibody-Directed Enzyme Prodrug Therapy (ADEPT)," *Drugs of the Future*, Vol. 21, p. 917.

Jungheim and Shepherd, 1994, "Design of Antitumour Prodrugs: Substrates for Antibody Targeted Enzymes," *Chemical Reviews*, Vol. 94, p. 1553.

Kim, D., 2000, "Replication-selective microbiological agents fighting cancer with targeted germ ware," Journal of Clinical Investigation (JCI), Vol. 105, No. 7, pp. 837–839.

Marais, R.; Spooner, R. A.; Stribbling, S. M.; Light, Y.; Martin, J.; Springer, C. J. S., 1997, "A cell surface tethered enzyme improves efficiency in gene-directed enzyme prodrug therapy," *Nature Biotechnology*, Vol. 15, pp. 1373–1377.

Martin, J.; Stribbling, S. M.; Poon, G. K.; Begent, R. H. J.; Napier, M.; Sharma, S. K.; Springer, C. J., 1997, "Antibody-directed enzyme prodrug therapy: Pharmacokinetics and plasma levels of prodrug and drug in a phase I clinical trial," *Cancer Chemotherapy and Pharmacology*, Vol. 40, pp. 189–201.

Matthews, 1988, "Structural Basis of the Action of Thermolysin and Related Zinc Peptidases," *Accounts of Chemical Research*, Vol. 21, p. 333.

Melton and Sherwood, 1996, "Antibody-Enzyme Conjugates for Cancer Therapy," *Journal of the National Cancer Institute*, Vol. 88, p 153.

Minton et al., 1984, "The Complete Nucleotide Sequence of the Pseudomonas Gene Coding for Carboxypeptidase G2," *Gene*, Vol. 31, p. 31.

Napier, M. P.; Sharma, S. K.; Springer, C. J.; Bagshawe, K. D.; Green, A. J.; Martin, J.; Stribbling, S. M.; Cushen, N.; O'Malley, D.; Begent, R. H. J., 2000, "Antibody-directed enzyme prodrug therapy: Efficacy and mechanism of action in colorectal carcinoma," *Clinical Cancer Research*, Vol. 6, pp. 765–772.

Niculescu-Duvaz and Springer, 1995, "Antibody-Directed Enzyme Prodrug Therapy (ADEPT): A Targeting Strategy in Chemotherapy," *Current Medicinal Chemistry*, Vol. 2, p. 687.

Niculescu-Duvaz and Springer, 1996, "Development of Prodrugs for ADEPT (Antibody-Directed Prodrug Therapy)," *Expert Opinion on Investigational Drugs*, Vol. 3, p. 289.

Niculescu-Duvaz and Springer, 1997, "Gene-Directed Enzyme Prodrug Therapy: A Review of Enzyme/Prodrug Combinations," *Expert Opinion on Investigational Drugs*, Vol. 6, p. 685.

Niculescu-Duvaz et al., 1998a, "Gene-Directed Enzyme Prodrug Therapy," *Bioconjugate Chemistry*, Vol. 9, p. 4.

Niculescu-Duvaz, D.; Niculescu-Duvaz, I.; Friedlos, F. F.; Martin, J.; Spooner, R.; Davies, L.; Marais, R.; Springer, C. J., 1998b, "Self-immolative mustard prodrugs for suicide gene therapy," *Journal of Medicinal Chemistry*, Vol. 41, pp. 5297–5309.

Niculescu-Duvaz et al., 1999a, "Recent Developments in Gene-Directed Enzyme Prodrug Therapy (GDEPT) for cancer," *Current Opinion in Molecular Therapeutics*, Vol. 1, p. 480.

Roswell et al., 1997, "Crystal Structure of Carboxypeptidase G2, a Bacterial Enzyme with Applications in Cancer Therapy," *Structure*, Vol. 5.

Roth and Cristiano, 1997, "Gene Therapy for Cancer: What Have We Done And Where Are We Going?," *Journal of the National Cancer Institute*, Vol. 89, p. 21.

Satchi and Duncan, 1998, "PDEPT: polymer-directed enzyme prodrug therapy," British Journal of Cancer, Vol. 78, No. 2, pp. 149–150.

Senter et al., 1993, "Generation of Cytotoxic Agents by Targeted Enzymes," *Bioconjugate Chemistry*, Vol. 4., p. 3.

Sherwood et al., 1985, "Purification and Properties of Carboxypeptidase G2 *Pseudomonas* sp strain RS-16," *European Journal of Biochemistry*, Vol. 148, p 447.

Spooner, R.; Martin, J.; Friedlos, F.; Marais, R.; Springer, C. J., 2000, "In suicide gene therapy, the site of subcellular localization of the activating enzyme is more important than the rate at which it activates prodrug," *Cancer Gene Therapy*, Vol. 7, pp. 1348–1356.

Springer and Marais, 1996a, "Intracellular Expression of Carboxypeptidase G2 in Enzyme Prodrug Therapy," published international (PCT) patent application number WO 96/03151 (PCT/GB95/01783), published 8 Feb. 1996.

Springer and Marais, 1996b, "Surface Expression of Enzyme in Gene Directed Prodrug Therapy," published international (PCT) patent application number WO 96/03515 (PCT/GB95/01782), published 8 Feb. 1996.

Springer and Marais, 1997, "Ligand Directed Enzyme Prodrug Therapy," published international (PCT) patent application number WO 97/26918 (PCT/GB97/00221), published 31 Jul. 1997.

Springer and Niculescu-Duvaz, 1995, "Antibody-Directed Enzyme Prodrug Therpay (ADEPT) with mustard prodrugs," *Anti-Cancer Drug Design*, Vol. 10, pp. 361–362.

Springer and Niculescu-Duvaz, 1999, "Patent Property of Prodrugs Involving Suicide Gene Therapy," *Expert Opinion on Therapeutic Patents*, Vol. 9, p. 1381.

Springer et al., 1990a, "Novel Prodrugs Which Are Activated to Cytotoxic Alkylating Agents by Carboxypeptidase G2," *Journal of Medicinal Chemistry*, Vol. 33, p. 677.

Springer et al., 1990b, "Improvements Relating to the Production of Prodrugs," published international (PCT) patent application number WO 90/02729, published 22 Mar. 1990.

Springer et al., 1991, "New Route of Synthesis for Tertiary Alkyl Esters," published international (PCT) patent application number WO 91/03460 published 21 Mar. 1991.

Springer et al., 1994, "4-Amino-Fluorobenzamides and Their Use as Cytotoxic Prodrugs," published international (PCT) patent application number WO 94/25429 published 10 Nov. 1994.

Springer et al., 1995a, "The Design of Prodrugs for Antibody Directed Enzyme Prodrug Therapy (ADEPT)," in *New Antibody Technologies and the Emergence of Useful Cancer Therapy*, Begent, R., Hamlin, A., editors (The Royal Society of Medicine Press: London), p. 75.

Springer et al., 1995b, "Optimization of Alkylating Prodrugs Derived from Phenol and Aniline Mustards: A New Clinical Candidate Prodrug (ZD2767) for ADEPT," *Journal of Medicinal Chemistry*, Vol. 38, p. 5051.

Springer et al., 1995c, "Prodrugs of Protein Tyrosine Kinase Inhibitors," published international (PCT) patent application number WO 95/02420, published 26 Jan. 1995.

Springer et al., 1995d, "Improvements Relating to Prodrugs," published international (PCT) patent application number WO 95/03830, published 9 Feb. 1995.

Springer et al., 1996, "Nitrogen Mustard Prodrugs with Novel Lipophilic Protecting Groups, and Processes for Their Production," published international (PCT) patent application number WO 96/22277, published 25 Jul. 1996.

Springer et al., 2000, "Nitrogen Mustard Compounds and Prodrugs Therefor," published international (PCT) patent application number WO 00/58271, published 5 Oct. 2000.

Springer et al., 2002, "Methods of Chemical Synthesis of Phenolic Nitrogen Mustard Prodrugs," published international (PCT) patent application number WO 02/060862 (PCT/GB02/00281), published 8 Aug. 2002.

Wakselman, 1983, "1,4 and 1,6 Eliminations from Hydroxy- and Amino-Substituted Benzyl Systems: Chemical and Biochemical Applications," *Nouveau Journal de Chemie*, Vol. 7, p. 439.

Zhang et al., 1995, "Advances in Cancer Gene Therapy," *Advances in Pharmacology*, Vol. 12, p. 289.

What is claimed is:

1. A compound of the formula:

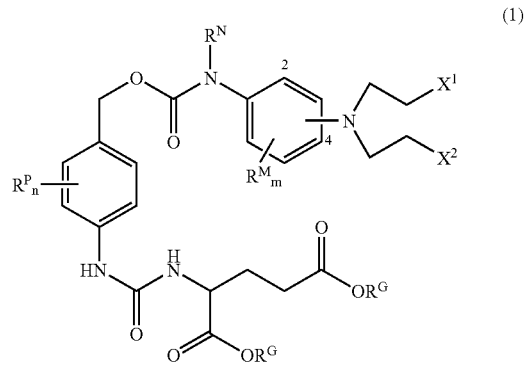

wherein:
$R^N$ is independently $C_{1-7}$alkyl;
$X^1$ is independently —I, —Br, or —Cl;
$X^2$ is independently —I, —Br, or —Cl;
the group —N(CH$_2$CH$_2$X$^1$)(CH$_2$CH$_2$X$^2$) is independently attached at the 2-position or at the 4-position;
each $R^G$ is independently —H or an ester substituent;
n is independently an integer from 0 to 4;
each $R^P$, if present, is independently a phenyl substituent;
m is independently an integer from 0 to 4;
each $R^M$, if present, is independently a mustard substituent;
and pharmaceutically acceptable salts, solvates, amides, and esters thereof.

2. A compound according to claim 1, wherein $R^N$ is independently unsubstituted al iphatic $C_{1-7}$alkyl.

3. A compound according to claim 1, wherein $R^N$ is independently unsubstituted al iphatic $C_{1-4}$alkyl.

4. A compound according to claim 1, wherein $R^N$ is independently -Me, -Et, -nPr, -iPr, -allyl, -nBu, -sBu, -iBu, or -tBu.

5. A compound according to claim 1, wherein $R^N$ is independently -Me or -Ft.

6. A compound according to claim 1, wherein $R^N$ is independently -Me.

7. A compound according to claim 1, wherein each of $X^1$ and $X^2$ is independently —I.

8. A compound according to claim 1, wherein each of $X^1$ and $X^2$ is independently —Br.

9. A compound according to claim 1, wherein each of $X^1$ and $X^2$ is independently —Cl.

10. A compound according to claim 1, wherein
$R^N$ is independently $C_{1-4}$alkyl; and,
each X is independently —Cl, —Br or —I.

11. A compound according to claim 1, wherein
$R^N$ is independently -Me; and,
each X is independently —Cl, —Br or —I.

12. A compound according to claim 1, wherein
$R^N$ is independently $C_{1-4}$alkyl; and,
each X is independently —I.

13. A compound according to claim 1, wherein
$R^N$ is independently -Et or -Me; and,
each X is independently —I.

14. A compound according to claim 1, wherein
$R^N$ is independently -Me; and,
each X is independently —I.

15. A compound according to claim 1, wherein the group —N(CH$_2$CH$_2$X$^1$)(CH$_2$CH$_2$X$^2$) is independently attached at the 4-position.

16. A compound according to claim 1, wherein
R$^N$ is independently C$_{1-4}$alkyl;
each X is independently —Cl, —Br or —I; and,
the group —N(CH$_2$CH$_2$X)$_2$ is independently attached at the 4-position.

17. A compound according to claim 1, wherein
R$^N$ is independently -Me;
each X is independently —Cl, —Br or —I; and,
the group —N(CH$_2$CH$_2$X)$_2$ is independently attached at the 4-position.

18. A compound according to claim 1, wherein
R$^N$ is independently C$_{1-4}$alkyl;
each X is independently —I; and,
the group —N(CH$_2$CH$_2$X)$_2$ is independently attached at the 4-position.

19. A compound according to claim 1, wherein
R$^N$ is independently -Et or -Me;
each X is independently —I; and,
the group —N(CH$_2$CH$_2$X)$_2$ is independently attached at the 4-position.

20. A compound according to claim 1, wherein
R$^N$ is independently -Me;
each X is independently —I; and,
the group —N(CH$_2$CH$_2$X)$_2$ is independently attached at the 4-position.

21. A compound according to claim 1, wherein n is 0, 1, or 2.

22. A compound according to claim 16, wherein n is 0.

23. A compound according to claim 1, wherein each R$^P$, if present, is independently halo, C$_{1-4}$alkyl, nitro, or cyano.

24. A compound according to claim 1, wherein each R$^P$, if present, is independently:
—F, —Cl, —Br, —I, -Me, -Et, -nPr, -iPr, -nBu, -sBu, -iBu, -tBu, —NO$_2$, or —CN.

25. A compound according to claim 1, wherein each R$^P$, if present, is independently —F, —Cl, —Br, or —I.

26. A compound according to claim 1, wherein m is 0, 1, or 2.

27. A compound according to claim 16, wherein m is 0.

28. A compound according to claim 22, wherein m is 0.

29. A compound according to claim 1, wherein each R$^M$, if present, is independently selected from: C$_{1-4}$alkyl; C$_{1-4}$alkoxy; amino; halo; C$_{1-4}$alkylthio; acyl; ester; amido; cyano; nitro; and, C$_{5-6}$aryl.

30. A compound according to claim 1, wherein each R$^M$, if present, is independently selected from:
-Me, -Et, -nPr, -iPr, -nBu, -sBu, -iBu, -tBu;
—CF$_3$, —CH$_2$F, —CH$_2$CF$_3$, —CH$_2$CH$_2$F; —CF$_2$CF$_3$;
—OMe, —OEt, —O-nPr, —O-iPr, —O-nBu, —O-sBu, —O-iBu, —O-tBu;
—OCF$_3$, —OCH$_2$F, —OCH$_2$CF$_3$, —OCH$_2$CH$_2$F; —OCF$_2$CF$_3$;
—NH$_2$, —NMe$_2$, —NEt$_2$, —N(nPr)$_2$, —N(iPr)$_2$;
—F, —Cl, —Br, —I;
—SMe, —SEt;
—C(=O)Me;
—C(=O)OMe, —C(=O)OEt;
—CONH$_2$, —CONHMe;
—CN;
—NO$_2$; and,
-Ph.

31. A compound according to claim 1, wherein each R$^M$, if present, is independently selected from:
-Me, -Et, —CF$_3$, —OMe, —OEt, —NH$_2$, and —NMe$_2$.

32. A compound according to claim 1, wherein each R$^G$ is independently —H.

33. A compound according to claim 1, wherein each R$^G$ is independently —H, unsubstituted C$_{1-7}$alkyl, substituted C$_{1-7}$alkyl, or silyl.

34. A compound according to claim 1, wherein each R$^G$ is independently —H; unsubstituted C$_{1-4}$alkyl; C$_{1-4}$alkyl substituted with one or more groups selected from optionally substituted C$_{5-20}$aryl, C$_{1-7}$alkoxy, C$_{1-7}$alkylthio, and acyloxy; or —SiR$^S$$_3$, wherein each R$^S$ is independently —H or C$_{1-4}$alkyl.

35. A compound according to claim 1, wherein each R$^G$ is independently —H; -Me; -Et; -nPr; -iPr; -allyl; -nBu; -sBu; -iBu; -tBu; C$_{1-4}$alkyl substituted with one or more groups selected from optionally substituted phenyl, methoxy, methylthio, acetoxy, and benzoyloxy; —Si(Me)$_3$; —Si(Et)$_3$; —Si(iPr)$_3$; —Si(tBu)(CH$_3$)$_2$; or —Si(tBu)$_3$.

36. A compound according to claim 1, wherein each R$^G$ is independently (1) t-butyl, (2) allyl, (3) tri-isopropylsilyl, (4) acetoxymethyl, (5) methoxymethyl, (6) methylthiomethyl, (7) p-methoxyphenylmethyl, (8) bis(o-nitrophenyl)methyl, (9) benzyl, or (10) diphenylmethyl.

37. A compound according to claim 1, wherein each R$^G$ is independently (1) t-butyl, (2) allyl, or (3) tri-isopropylsilyl.

38. A compound according to claim 1, wherein each R$^G$ is independently (1) allyl.

39. A compound selected from compounds of the following formula (P-1), and pharmaceutically acceptable salts, solvates, amides, and esters thereof:

40. A compound selected from compounds of the following formula (P-2), and pharmaceutically acceptable salts, solvates, amides, and esters thereof:

41. A compound selected from compounds of the following formula (P-3), and pharmaceutically acceptable salts, solvates, amides, and esters thereof:

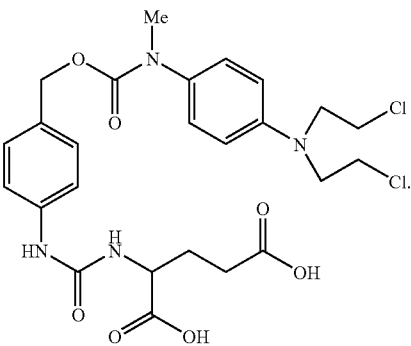

42. A composition comprising a compound according to claim 1, and a pharmaceutically acceptable carrier.

43. A kit comprising:
(a) a compound according to claim 1; and
(b) instructions for use.

44. A kit comprising:
(a) a compound according to claim 1;
(b) an antibody or fragment thereof conjugated or fused to a carboxypeptidase enzyme; and,
(c) instructions for use.

45. A kit comprising:
(a) a compound according to claim 1;
(b) a nucleic acid encoding a carboxypeptidase enzyme; and,
(c) instructions for use.

46. A method of inhibiting cell cycle progression of a cell, in vitro or in vivo, comprising contacting the cell with an effective amount of a compound according to claim 1.

47. A method of treatment of colon cancer comprising administering to a subject in need of treatment a therapeutically-effective amount of a compound according to claim 1.

48. A method of inhibiting cell cycle progression of a cell, in vitro or in vivo, comprising contacting the cell with a therapeutically-effective amount of a compound according to claim 1, in the presence of a carboxypeptidase enzyme.

49. A method of treatment of colon cancer comprising administering to a subject in need of treatment a therapeutically-effective amount of a compound according to claim 1, in the presence of a carboxypeptidase enzyme.

50. A method of inhibiting cell cycle progression of a cell, in vitro or in vivo, comprising:
(i) contacting the cell with an antibody or fragment thereof conjugated or fused to a carboxypeptidase enzyme; and,
(ii) contacting the cell with a therapeutically-effective amount of a compound according to claim 1.

51. A method of treatment of colon cancer, comprising administering to a subject in need of treatment:
(i) an antibody or fragment thereof conjugated or fused to a carboxypeptidase enzyme; and,
(ii) contacting the cell with a therapeutically-effective amount of a compound according to claim 1.

52. A method of inhibiting cell cycle progression of a cell, in vitro or in vivo, comprising:
(i) contacting the cell with a nucleic acid encoding a carboxypeptidase enzyme; and,
(ii) contacting the cell with a therapeutically-effective amount of a compound according to claim 1.

53. A method of treatment of colon cancer, comprising administering to a subject in need of treatment:
(i) a nucleic acid encoding a carboxypeptidase enzyme; and,
(ii) a therapeutically-effective amount of a compound according to claim 1.

* * * * *